(12) United States Patent
Han et al.

(10) Patent No.: US 11,341,734 B2
(45) Date of Patent: May 24, 2022

(54) SYSTEMS AND METHODS FOR IMAGE SEGMENTATION

(71) Applicant: SHANGHAI UNITED IMAGING INTELLIGENCE CO., LTD., Shanghai (CN)

(72) Inventors: Miaofei Han, Shanghai (CN); Yu Zhang, Shanghai (CN); Yaozong Gao, Shanghai (CN); Yiqiang Zhan, Shanghai (CN)

(73) Assignee: SHANGHAI UNITED IMAGING INTELLIGENCE CO., LTD., Shanghai (CN)

( * ) Notice: Subject to any disclaimer, the term of this patent is extended or adjusted under 35 U.S.C. 154(b) by 2 days.

(21) Appl. No.: 16/870,905

(22) Filed: May 9, 2020

(65) Prior Publication Data
US 2020/0272841 A1    Aug. 27, 2020

Related U.S. Application Data

(63) Continuation of application No. PCT/CN2019/128679, filed on Dec. 26, 2019.

(30) Foreign Application Priority Data

Dec. 28, 2018 (CN) .......................... 201811622330.9

(51) Int. Cl.
*G06V 10/22* (2022.01)
*G06T 7/62* (2017.01)
(Continued)

(52) U.S. Cl.
CPC ............ *G06V 10/22* (2022.01); *A61B 5/1073* (2013.01); *G06K 9/6256* (2013.01); *G06N 3/04* (2013.01);
(Continued)

(58) Field of Classification Search
CPC ................................ A61B 5/1073; G06N 3/04
See application file for complete search history.

(56) References Cited

U.S. PATENT DOCUMENTS

| 5,274,580 A | 12/1993 | Keryvel et al. |
| 6,155,653 A | 12/2000 | Borchert |

(Continued)

FOREIGN PATENT DOCUMENTS

| CN | 101721751 A | 6/2010 |
| CN | 102253207 A | 11/2011 |

(Continued)

OTHER PUBLICATIONS

Machine translation of CN104156960 A, accessed Aug. 2021, google patents, pp. 1-7 (Year: 2021).*

(Continued)

*Primary Examiner* — Edward Park
(74) *Attorney, Agent, or Firm* — Metis IP LLC

(57) ABSTRACT

A system for image segmentation is provided. The system may obtain a target image including an ROI, and segment a preliminary region representative of the ROI from the target image using a first ROI segmentation model corresponding to a first image resolution. The system may segment a target region representative of the ROI from the preliminary region using a second ROI segmentation model corresponding to a second image resolution. At least one model of the first and second ROI segmentation models may at least include a first convolutional layer and a second convolutional layer downstream to the first convolutional layer. A count of input channels of the first convolutional layer may be greater than a count of output channels of the first convolutional layer, and a count of input channels of the second convolutional layer may be smaller than a count of output channels of the second convolutional layer.

20 Claims, 23 Drawing Sheets

(51) Int. Cl.

| | | |
|---|---|---|
| *G06T 7/11* | (2017.01) | |
| *G06T 7/149* | (2017.01) | |
| *G16H 50/50* | (2018.01) | |
| *G16H 50/30* | (2018.01) | |
| *G16H 50/20* | (2018.01) | |
| *G16H 30/40* | (2018.01) | |
| *A61B 5/107* | (2006.01) | |
| *G06K 9/62* | (2022.01) | |
| *G06N 3/04* | (2006.01) | |
| *G06V 30/24* | (2022.01) | |

(52) U.S. Cl.
CPC ............... *G06T 7/11* (2017.01); *G06T 7/149* (2017.01); *G06T 7/62* (2017.01); *G06V 30/2504* (2022.01); *G16H 30/40* (2018.01); *G16H 50/20* (2018.01); *G16H 50/30* (2018.01); *G16H 50/50* (2018.01); *A61B 2576/02* (2013.01); *G06T 2207/30084* (2013.01); *G06V 2201/031* (2022.01); *G06V 2201/032* (2022.01)

(56) References Cited

U.S. PATENT DOCUMENTS

| | | | |
|---|---|---|---|
| 9,943,223 | B2 | 4/2018 | Vazquez |
| 2013/0065239 | A1 | 3/2013 | Bodavilla Sandoval et al. |
| 2013/0279777 | A1 | 10/2013 | Serlie |
| 2015/0025372 | A1* | 1/2015 | Ghosh ............... G06K 9/3233 600/431 |
| 2015/0154756 | A1 | 6/2015 | Gerganov et al. |
| 2016/0068601 | A1 | 3/2016 | Brogdon et al. |
| 2017/0040016 | A1 | 2/2017 | Cui et al. |
| 2018/0189643 | A1 | 7/2018 | Kim et al. |
| 2018/0189953 | A1 | 7/2018 | Nie et al. |
| 2018/0285715 | A1 | 10/2018 | Son et al. |
| 2019/0377930 | A1 | 12/2019 | Chen et al. |
| 2020/0074288 | A1 | 3/2020 | Zhang et al. |
| 2020/0104642 | A1 | 4/2020 | Wei et al. |

FOREIGN PATENT DOCUMENTS

| | | | |
|---|---|---|---|
| CN | 102429679 | A | 5/2012 |
| CN | 103310458 | A | 9/2013 |
| CN | 104099918 | A | 10/2014 |
| CN | 104156960 | A * | 11/2014 |
| CN | 106709441 | A | 5/2017 |
| CN | 107067333 | A | 8/2017 |
| CN | 107155110 | A | 9/2017 |
| CN | 107578054 | A | 1/2018 |
| CN | 107766894 | A | 3/2018 |
| CN | 108304921 | A | 7/2018 |
| CN | 108564116 | A | 9/2018 |
| CN | 108682015 | A | 10/2018 |
| CN | 108764471 | A | 11/2018 |
| CN | 109035197 | A | 12/2018 |
| CN | 109583576 | A | 4/2019 |
| CN | 109754394 | A | 5/2019 |
| CN | 108304921 | B * | 2/2021 |
| WO | 2017062882 | A1 | 4/2017 |

OTHER PUBLICATIONS

Machine translation of CN108304921 B, accessed Aug. 2021, google patents, pp. 1-12 (Year: 2021).*
Hai Jin et al., Layer-Centric Memory Reuse and Data Migration for Extreme-Scale Deep Learning on Many-Core Architectures, ACM Transactions on Architecture and Code Optimization, 15(3):1-26, 2018.
HYC3140, CT cases of polycystic kidney disease, 2009, 3 pages, Retrieval: http://www.xctmr.com/abdomen/kidney/2009-01-21/478.html.
Baidubaike, Polycystic kidney, Baidu, 2020, 12 pages, Retrieval: https://baike.baidu.com/item/%E5%A4%9A%E5%9B%8A%E8%82%BE/270493?fr=aladdin.
Laureano J. Rangel et al., Imaging Classification of Autosomal Dominant Polycystic Kidney Disease: A Simple Model for Selecting Patients for Clinical Trials, Journal of the American Society of Nephrology, 26(1): 1-13, 2014.
Fausto Milletari et al., V-Net: Fully Convolutional Neural Networks for Volumetric Medical Image Segmentation, IEEE Computer Society, 2016, 11 pages.
Deng, Yan, Research on the Registration and Storage Techniques for Medical Microscopic Images, Chinese Doctoral Dissertation Full-text Database, 2013, 113 pages.
Kim Francis Andersen et al., Volume-Based F-18 FDG PET/CT Imaging Markers Provide Supplemental Prognostic Information to Histologic Grading in Patients With High-Grade Bone or Soft Tissue Sarcoma, Medicine, 2015, 7 pages.
Gao, Zhenyu, Research and application of image classification method based on deep convolutional neural network, Chinese Doctoral Dissertation Full-text Database, 2018, 114 pages.
International Search Report in PCT/CN2019/128679 dated Mar. 26, 2020, 4 pages.
Written Opinion in PCT/CN2019/128679 dated Mar. 26, 2020, 5 pages.
First Office Action in Chinese Application No. 201811544139.7 dated Apr. 27, 2020, 19 pages.
First Office Action in Chinese Application No. 201811622330.9 dated May 27, 2020, 17 pages.

* cited by examiner

1400

1410

1420

1400

1440

1450

1460

1400

1470

1417 1418

1500

1510

1520

1522

1524

1530

1540

1550

1560

1500

1572

1700

1800

SYSTEMS AND METHODS FOR IMAGE SEGMENTATION

CROSS-REFERENCE TO RELATED APPLICATIONS

This application is a continuation of International Patent Application PCT/CN2019/128679, filed on Dec. 26, 2019, which claims priority to Chinese Patent Application No. 201811622330.9, filed on Dec. 28, 2018, and Chinese Patent Application No. 201811544139.7, filed on Dec. 17, 2018, the contents of each of which are hereby incorporated by reference.

TECHNICAL FIELD

The present disclosure generally relates to image processing, and in particular, to systems and methods for image segmentation.

BACKGROUND

Medical imaging techniques, such as a magnetic resonance imaging (MRI) technique, a computed tomography (CT) imaging technique, or the like, have been widely used for disease diagnosis and treatment. In some occasions, an image of an object may be acquired according to a medical imaging technique, and a region of interest (ROI), such as a region representing a specific organ, may need to be segmented from the image. For example, a left kidney and a right kidney of a patient having polycystic kidney disease may be segmented from an MRI image of the patient for further analysis based on a manual input of a doctor. Merely by way of example, the kidneys of the patient may be regarded as having a shape of ellipse, the doctor may need to annotate the long axis and the short axis of the ellipse, and a computing device may determine the volume of the kidneys based on the doctor's annotation. This may be time-consuming (e.g., cost about 7 minutes) and inefficient. Recently, machine learning has promoted the development of computer-aided image segmentation. Normally, a neural network model and related files may occupy a large memory space (e.g., 250 MB) and have high requirements on electronic hardware. Therefore, it may be desirable to provide systems and methods for generating an ROI segmentation model and/or for using the ROI segmentation model that improves the accuracy and efficiency of image segmentation and saves time and resources.

SUMMARY

According to an aspect of the present disclosure, a system for image segmentation is provided. The system may include at least one storage device including a set of instructions and at least one processor configured to communicate with the at least one storage device. When executing the set of instructions, the at least one processor may be configured to direct the system to perform the following operations. The system may obtain a target image including an ROI, and segment a preliminary region representative of the ROI from the target image using a first ROI segmentation model corresponding to a first image resolution. The system may also segment a target region representative of the ROI from the preliminary region using a second ROI segmentation model corresponding to a second image resolution. The first image resolution may be lower than the second image resolution. At least one model of the first ROI segmentation model or the second ROI segmentation model may include a plurality of convolutional layers. The plurality of convolutional layers may at least include a first convolutional layer and a second convolutional layer downstream to the first convolutional layer. A count of input channels of the first convolutional layer may be greater than a count of output channels of the first convolutional layer, and a count of input channels of the second convolutional layer may be smaller than a count of output channels of the second convolutional layer.

In some embodiments, the system may determine a parameter value indicative of a physiological condition of the ROI based on the target region. The system may further evaluate the physiological condition of the ROI based on the parameter value.

In some embodiments, the ROI may include a polycystic kidney. The parameter value may include a volume of the polycystic kidney. To evaluate a physiological condition of the ROI based on the volume of the ROI, the system may classify a functionality of the polycystic kidney based at least in part on the volume of the polycystic kidney.

In some embodiments, to segment a preliminary region representative of the ROI from the target image, the system may preprocess the target image, and segment the ROI from the preprocessed target image by applying the first ROI segmentation model to the preprocessed target image. The system may further segment the preliminary region from the target image based on the segmented ROI in the preprocessed target image.

In some embodiments, to preprocess the target image, the system may generate a resampled target image having the first image resolution by resampling the target image, and generate the preprocessed target image by normalizing the resampled target image.

In some embodiments, to segment a target region representative of the ROI from the preliminary region, the system may preprocess the preliminary region, and segment the ROI from the preprocessed preliminary region by applying the second ROI segmentation model to the preprocessed preliminary region. The system may also generate the target region by resampling the segmented ROI in the preprocessed preliminary region. The target region and the target image may have a same image resolution.

In some embodiments, to preprocess the preliminary region, the system may generate a resampled preliminary region having the second image resolution by resampling the preliminary region, and generate the preprocessed preliminary region by normalizing the resampled preliminary region.

In some embodiments, the at least one model may be one of a V-net model, a U-net model, an AlexNet model, an Oxford Visual Geometry Group (VGG) model, or a ResNet model.

In some embodiments, the count of input channels of the first convolutional layer may be equal to the count of output channels of the second convolutional layer.

In some embodiments, the at least one model may further include a third convolutional layer between the first convolutional layer and the second convolutional layer. A count of output channels of the third convolutional layer may be equal to a count of input channels of the third convolutional layer.

In some embodiments, the system may determine a first memory space and a second memory space in the at least one storage device based on the plurality of convolutional layers. The plurality of convolutional layers may include a fourth convolutional layer and a fifth convolutional layer adjacent to each other. During the application of at least one model, input data of the fourth convolutional layer may be stored in the first memory space. Output data of the fourth convolutional layer may be stored in the second memory. Input data of the fifth convolutional layer may be stored in the second memory space. Output data of the fifth convolutional layer may be stored in the first memory.

In some embodiments, the at least one model may include at least one skip-connection, and data relating to the at least one skip-connection may be stored in at least one of the first memory space or the second memory space.

According to another aspect of the present disclosure, a system for training an ROI segmentation model corresponding to a target image resolution is provided. The system may include at least one storage device storing a set of instructions and at least one processor configured to communicate with the at least one storage device. When executing the set of instructions, the system may obtain at least one training image. Each of the at least one training image may include an annotated ROI and have the target image resolution. The system may also obtain a preliminary model including a plurality of convolutional layers. The system may further generate the ROI segmentation model corresponding to the target image resolution by training the preliminary model using the at least one training image. The plurality of convolutional layers may include at least a first convolutional layer and a second convolutional layer downstream to the first convolutional layer. A count of input channels of the first convolutional layer may be greater than a count of output channels of the first convolutional layer. A count of input channels of the second convolutional layer may be smaller than a count of output channels of the second convolutional layer.

In some embodiments, to acquire at least one training image, the system may obtain at least one image including an annotated ROI and having an image resolution different from the target image resolution. The system may also generate at least one resampled image having the target image resolution by resampling the at least one image, and generate the at least one training image by normalizing the at least one resampled image.

In some embodiments, the count of input channels of the first convolutional layer may be equal to the count of the output channels of the second convolutional layer.

In some embodiments, the plurality of convolutional layers may further include a third convolutional layer between the first convolutional layer and the second convolutional layer, and a count of output channels of the third convolutional layer may be equal to a count of input channels of the third convolutional layer.

In some embodiments, the preliminary model may include at least one of a V-net model, a U-net model, an AlexNet model, an Oxford Visual Geometry Group (VGG) model, or a ResNet model.

According to yet another aspect of the present disclosure, a method for image segmentation may be provided. The method may be implemented on a computing device having at least one processor and at least one storage device. The method may include obtaining a target image including an ROI, and segmenting a preliminary region representative of the ROI from the target image using a first ROI segmentation model corresponding to a first image resolution. The method may also include segmenting a target region representative of the ROI from the preliminary region using a second ROI segmentation model corresponding to a second image resolution. The first image resolution may be lower than the second image resolution. At least one model of the first ROI segmentation model or the second ROI segmentation model may include at least a first convolutional layer and a second convolutional layer downstream to the first convolutional layer. A count of input channels of the first convolutional layer may be greater than a count of output channels of the first convolutional layer, and a count of input channels of the second convolutional layer may be smaller than a count of output channels of the second convolutional layer.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
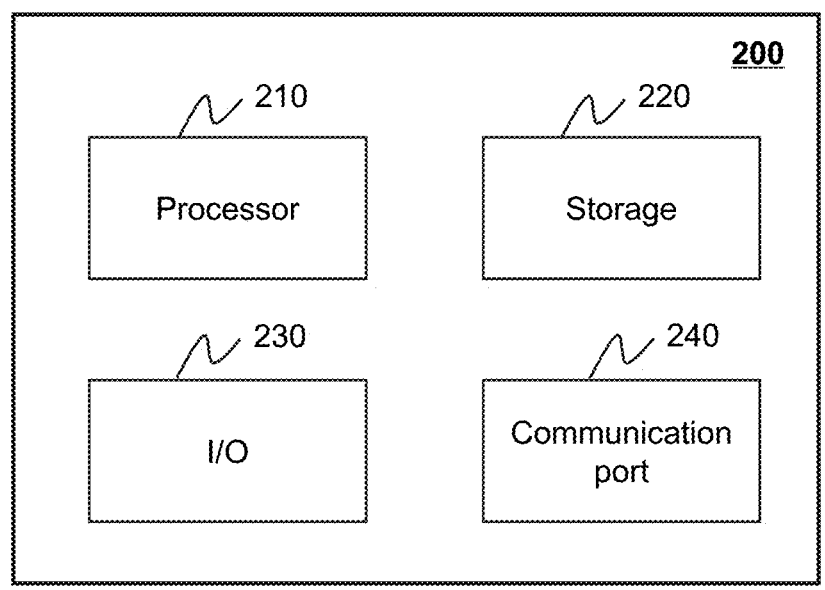
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for non-invasive biomedical imaging, such as for disease diagnostic or research purposes. In some embodiments, the systems may include a single modality imaging system and/or a multi-modality imaging system. The single modality imaging system may include, for example, an ultrasound imaging system, an X-ray imaging system, an computed tomography (CT) system, a magnetic resonance imaging (MRI) system, an ultrasonography system, a positron emission tomography (PET) system, an optical coherence tomography (OCT) imaging system, an ultrasound (US) imaging system, an intravascular ultrasound (IVUS) imaging system, a near infrared spectroscopy (NIRS) imaging system, or the like, or any combination thereof. The multi-modality imaging system may include, for example, an X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a positron emission tomography-computed tomography (PET-CT) system, a C-arm system, a digital subtraction angiography-magnetic resonance imaging (DSA-MRI) system, etc. It should be noted that the imaging system described below is merely provided for illustration purposes, and not intended to limit the scope of the present disclosure.

The term "imaging modality" or "modality" as used herein broadly refers to an imaging method or technology that gathers, generates, processes, and/or analyzes imaging information of an object. The object may include a biological object and/or a non-biological object. The biological object may be a human being, an animal, a plant, or a portion thereof (e.g., a cell, a tissue, an organ, etc.). In some embodiments, the object may be a man-made composition of organic and/or inorganic matters that are with or without life.

Moreover, while the systems and methods disclosed in the present disclosure are described primarily regarding segmenting an ROI in an image in a medical imaging system. It should be understood that this is only one exemplary embodiment. The systems and methods of the present disclosure may be applied to any other kind of systems. For example, the systems and methods of the present disclosure may be applied to segment ROIs in images acquired in different scenarios and/or for different purposes (e.g., safety monitoring, filming, or photography) and/or by different image acquisition devices (e.g., a digital camera, an analog camera, or a scanner).

An aspect of the present disclosure relates to systems and methods for image segmentation. The systems and methods may obtain a target image including an ROI, and segment a preliminary region representative of the ROI from the target image using a first ROI segmentation model corresponding to a first image resolution. The systems and methods may further segment a target region representative of the ROI from the preliminary region using a second ROI segmentation model corresponding to a second image resolution. The first image resolution may be lower than the second image resolution. In other words, the preliminary region may be segmented from the target image at a relatively coarse resolution, and the target region may be subsequently refined from the preliminary region at a relatively fine resolution. The preliminary region may have a smaller size than the original target image such that the image segmentation methods disclosed herein may improve the efficiency of the process by reducing, e.g., the processing time, the computational complexity and/or cost, etc. For example, the segmentation methods disclosed herein may need a few seconds (e.g., 1.2 seconds) to segment the target region, which is more efficient than conventional manual segmentation methods.

According to some embodiments of the present disclosure, an ROI segmentation model corresponding to a certain image resolution may be a CNN model in which a convolutional layer is replaced by a Bottleneck structure. For example, the ROI segmentation model may include at least a first convolutional layer and a second convolutional layer downstream to the first convolutional layer, wherein a count of input channels of the first convolutional layer may be greater than a count of output channels of the first convolutional layer, and a count of input channels of the second convolutional layer may be smaller than a count of output channels of the second convolutional layer. The ROI segmentation model with a Bottleneck structure may have fewer model parameters and/or need less storage space than the original CNN model, thereby saving operation resources and improving system efficiency. In some embodiments, the ROI segmentation model may be a V-net model incorporating one or more Bottleneck structures, which may extract features of an input image at different scales (or image resolutions) and have a high image segmentation accuracy.

Moreover, in some embodiments, during the application of an ROI segmentation model, a memory utilization strategy may be adopted by the systems and methods disclosed in the present disclosure. Merely by way of example, a first memory space and a second memory space may be used alternatively and repeatedly during the application of the ROI segmentation model. For instance, for a pair of convolutional layers adjacent to each other in the ROI segment model, the input of one of the pair of convolutional layers may occupy a first memory space, the output of the one of the pair of convolutional layers may occupy a second memory space, while the input of the other one of the pair of convolutional layers may occupy the second memory space, and the output of the other one of the pair of convolutional layers may occupy the first memory space. Optionally, if the ROI segmentation model includes a skip connection, data relating to the skip connection (e.g., input and output of convolutional layers connected by the skip connection) may be stored in at least one of the first memory space or the second memory space. This may reduce the needed memory space and improve the efficiency of the model application.

Figure 1:
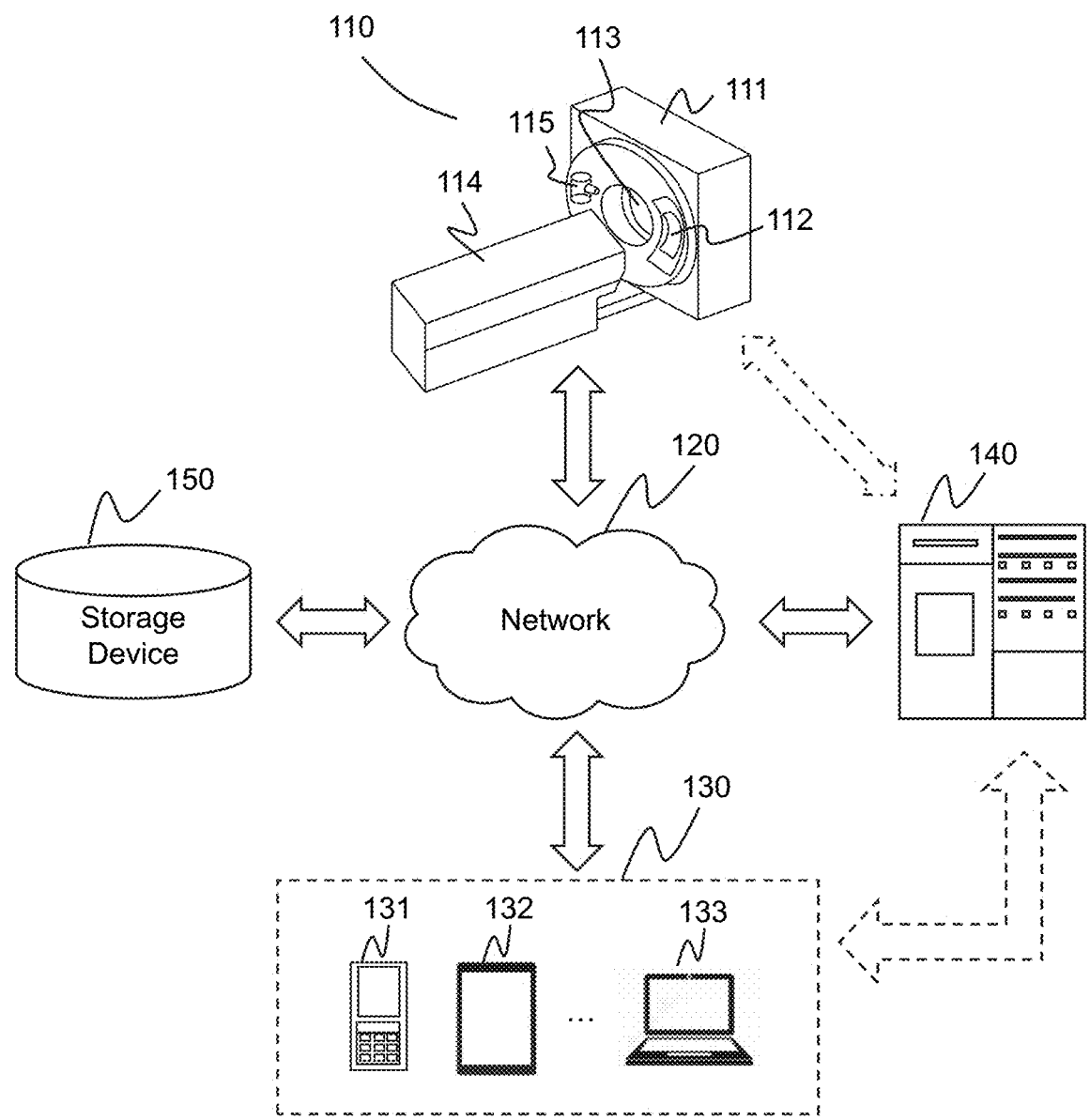
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. As illustrated in FIG. 1, the imaging system 100 may include an imaging device 110, a network 120, one or more terminals 130, a processing device 140, and a storage device 150. The components in the imaging system 100 may be connected in one or more of various ways. Merely by way of example, the imaging device 110 may be connected to the processing device 140 through the network 120. As another example, the imaging device 110 may be connected to the processing device 140 directly as indicated by the bi-directional arrow in dotted lines linking the imaging device 110 and the processing device 140. As a further example, the storage device 150 may be connected to the processing device 140 directly or through the network 120. As still a further example, the terminal 130 may be connected to the processing device 140 directly (as indicated by the bi-directional arrow in dotted lines linking the terminal 130 and the processing device 140) or through the network 120.

The imaging device 110 may generate or provide image data related to an object via scanning the object. In some embodiments, the object may include a biological object and/or a non-biological object. For example, the object may include a specific portion of a body, such as a head, a thorax, an abdomen, or the like, or a combination thereof. In some embodiments, the imaging device 110 may include a single-modality scanner (e.g., a CT scanner) and/or multi-modality scanner (e.g., a PET-CT scanner) as described elsewhere in this disclosure. In some embodiments, the image data relating to the object may include projection data, one or more images of the object, etc. The projection data may include raw data generated by the imaging device 110 by scanning the object and/or data generated by a forward projection on an image of the object.

In some embodiments, the imaging device 110 may include a gantry 111, a detector 112, a detecting region 113, a scanning table 114, and a radioactive scanning source 115. The gantry 111 may support the detector 112 and the radioactive scanning source 115. The object may be placed on the scanning table 114 to be scanned. The radioactive scanning source 115 may emit radioactive rays to the object. The radiation may include a particle ray, a photon ray, or the like, or a combination thereof. In some embodiments, the radiation may include a plurality of radiation particles (e.g., neutrons, protons, electron, μ-mesons, heavy ions), a plurality of radiation photons (e.g., X-ray, a γ-ray, ultraviolet, laser), or the like, or a combination thereof. The detector 112 may detect radiations and/or radiation events (e.g., gamma photons) emitted from the detecting region 113. In some embodiments, the detector 112 may include a plurality of detector units. The detector units may include a scintillation detector (e.g., a cesium iodide detector) or a gas detector. The detector unit may be a single-row detector or a multi-rows detector.

The network 120 may facilitate exchange of information and/or data. In some embodiments, one or more components of the imaging system 100 (e.g., the imaging device 110, the terminal 130, the processing device 140, or the storage device 150) may send information and/or data to another component(s) of the imaging system 100 via the network 120. For example, the processing device 140 may obtain, via the network 120, one or more images from the storage device 150. In some embodiments, the network 120 may be any type of wired or wireless network, or combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired or wireless network access points such as base stations and/or internet exchange points through which one or more components of the imaging system 100 may be connected to the network 120 to exchange data and/or information.

The terminal 130 include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the terminal 130 may remotely operate the imaging device 110. In some embodiments, the terminal 130 may operate the imaging device 110 via a wireless connection. In some embodiments, the terminal 130 may receive information and/or instructions inputted by a user, and send the received information and/or instructions to the imaging device 110 or to the processing device 140 via the network 120. In some embodiments, the terminal 130 may receive data and/or information from the processing device 140. In some embodiments, the terminal 130 may be omitted or be part of the processing device 140.

In some embodiments, the processing device 140 may process data obtained from the imaging device 110, the terminal 130, or the storage device 150. For example, the processing device 140 may perform image segmentation on an image obtained from the imaging device 110 and/or the storage device 150. The processing device 140 may be a central processing unit (CPU), a digital signal processor (DSP), a system on a chip (SoC), a microcontroller unit (MCU), or the like, or any combination thereof.

The processing device 140 may process data and/or information obtained from the imaging device 110, the storage device 150, the terminal(s) 130, or other components of the imaging system 100. In some embodiments, the processing device 140 may be a single server or a server group. The server group may be centralized or distributed. For example, the processing device 140 may obtain or generate a plurality of training images for training an ROI segmentation model. The processing device 140 may further generate the ROI segmentation model by training a preliminary model using the training samples. As another example, the processing device 140 may apply the ROI segmentation model to a target image to perform ROI segmentation in the target image. In some embodiments, the training images and/or the ROI segmentation model may be generated by a processing device, while the application of the ROI segmentation model may be performed on a different processing device. In some embodiments, the training images and/or the ROI segmentation model may be generated by a processing device of a system different from the imaging system 100 or a server different from the processing device 140 on which the application of ROI segmentation model is performed. For instance, the training images and/or the ROI segmentation model may be generated by a first system of a vendor who provides and/or maintains such an ROI segmentation model, while ROI segmentation on a target image based on the provided ROI segmentation model may be performed on a second system of a client of the vendor. In some embodiments, the application of the ROI segmentation model may be performed online in response to a request for ROI segmentation in a target image. In some embodiments, the training samples and/or the ROI segmentation model may be determined or generated offline.

In some embodiments, the ROI segmentation model may be determined and/or updated (or maintained) by, e.g., the manufacturer of the imaging device 110 or a vendor. For instance, the manufacturer or the vendor may load the ROI segmentation model into the imaging system 100 or a portion thereof (e.g., the processing device 140) before or during the installation of the imaging device 110 and/or the processing device 140, and maintain or update the ROI segmentation model from time to time (periodically or not). The maintenance or update may be achieved by installing a program stored on a storage device (e.g., a compact disc, a USB drive, etc.) or retrieved from an external source (e.g., a server maintained by the manufacturer or vendor) via the network 120. The program may include a new model (e.g., a new ROI segmentation model) or a portion of a model that substitute or supplement a corresponding portion of the model.

In some embodiments, the processing device 140 may be local or remote. For example, the processing device 140 may access information and/or data stored in the imaging device 110, the terminal 130, and/or the storage device 150 via the network 120. As another example, the processing device 140 may be directly connected to the imaging device 110, the terminal 130, and/or the storage device 150, to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal 130 and/or the processing device 140. For example, the storage device 150 may store one or more images obtained from the processing device 140 and/or the imaging device 110. In some embodiments, the storage device 150 may store data and/or instructions that the processing device 140 may execute or use to perform exemplary methods described in the present disclosure. For example, the storage device 150 may store data and/or instructions that the processing device 140 may execute or use to segment an ROI from an image. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the imaging system 100 (e.g., the terminal 130, the processing device 140). One or more components of the imaging system 100 may access the data or instructions stored in the storage device 150 via the network 120. In some embodiments, the storage device 150 may be directly connected to or communicate with one or more components of the imaging system 100 (e.g., the terminal 130, the processing device 140). In some embodiments, the storage device 150 may be part of the processing device 140.

It should be noted that the above description of the imaging system 100 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the imaging system 100 may include one or more additional components. Additionally or alternatively, one or more components of the imaging system 100 described above may be omitted. As another example, two or more components of the imaging system 100 may be integrated into a single component.

FIG. 2 is a schematic diagram illustrating hardware and/or software components of an exemplary computing device 200 according to some embodiments of the present disclosure. The computing device 200 may be used to implement any component of the imaging system 100 as described herein. For example, the processing device 140 and/or the terminal 130 may be implemented on the computing device 200, respectively, via its hardware, software program, firmware, or a combination thereof. Although only one such computing device is shown, for convenience, the computer functions relating to the imaging system 100 as described herein may be implemented in a distributed fashion on a number of similar platforms, to distribute the processing load.

As illustrated in FIG. 2, the computing device 200 may include a processor 210, a storage 220, an input/output (I/O) 230, and a communication port 240. The processor 210 may execute computer instructions (program code) and, when executing the instructions, cause the processing device 140 to perform functions of the processing device 140 in accordance with techniques described herein. The computer instructions may include, for example, routines, programs, objects, components, signals, data structures, procedures, modules, and functions, which perform particular functions described herein. In some embodiments, the processor 210 may process data and/or images obtained from the imaging device 110, the terminal 130, the storage device 150, and/or any other component of the imaging system 100. For example, the processor 210 may obtain a plurality of training images from the storage device 150, and generate an ROI segmentation model by training a preliminary model using the plurality of training images. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes process A and a second processor executes process B, or the first and second processors jointly execute operations A and B).

The storage 220 may store data/information obtained from the imaging device 110, the terminal 130, the storage device 150, or any other component of the imaging system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure.

The I/O 230 may input or output signals, data, and/or information. In some embodiments, the I/O 230 may enable user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the imaging device 110, the terminal 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMAX, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
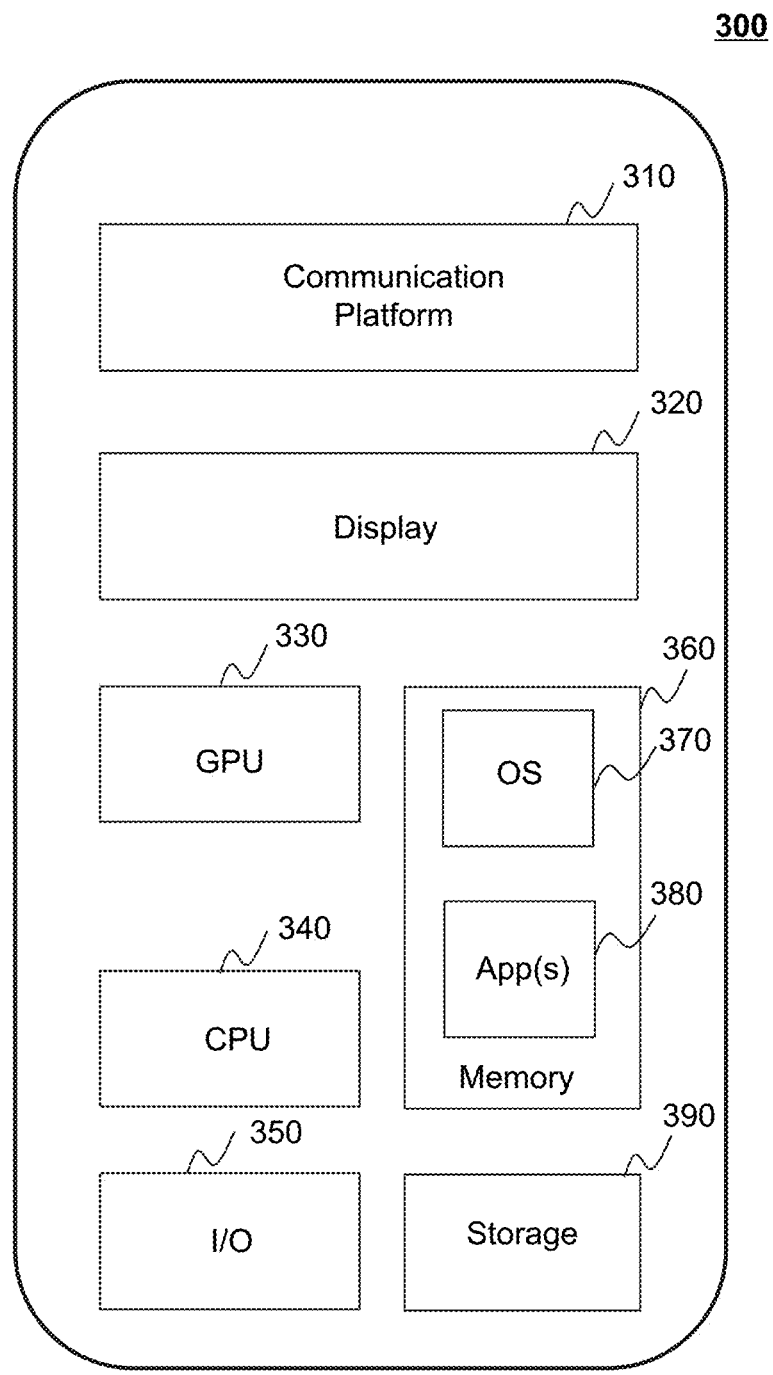
FIG. 3 is a schematic diagram illustrating hardware and/or software components of an exemplary mobile device according to some embodiments of the present disclosure.

FIG. 3 is a schematic diagram illustrating hardware and/or software components of a mobile device 300 according to some embodiments of the present disclosure. In some embodiments, the processing device 140 and/or the terminal 130 may be implemented on the mobile device 300. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to the imaging system 100 from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate a high-quality image of an object as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4A:
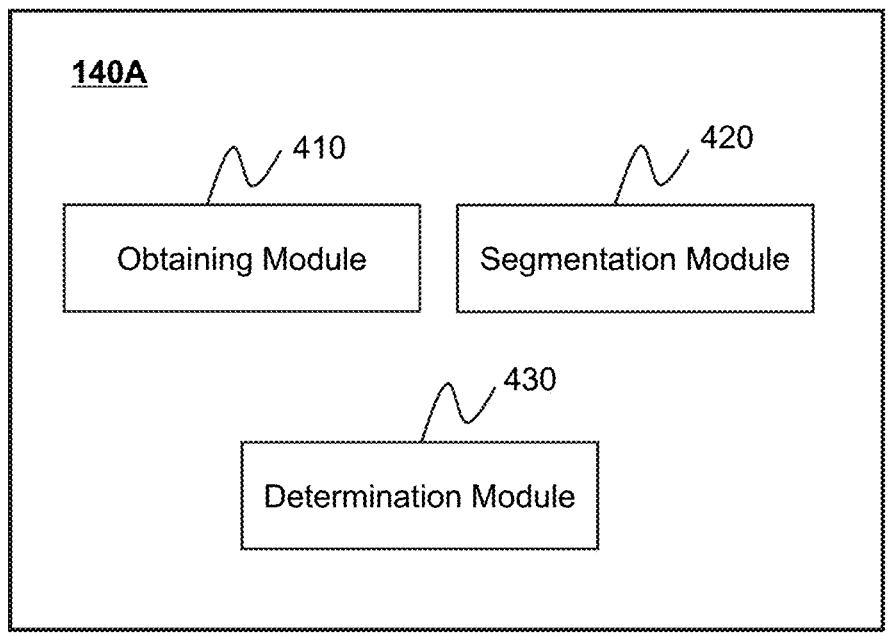
FIGS. 4A and 4B are block diagrams illustrating exemplary processing devices according to some embodiments of the present disclosure.
Figure 4B:
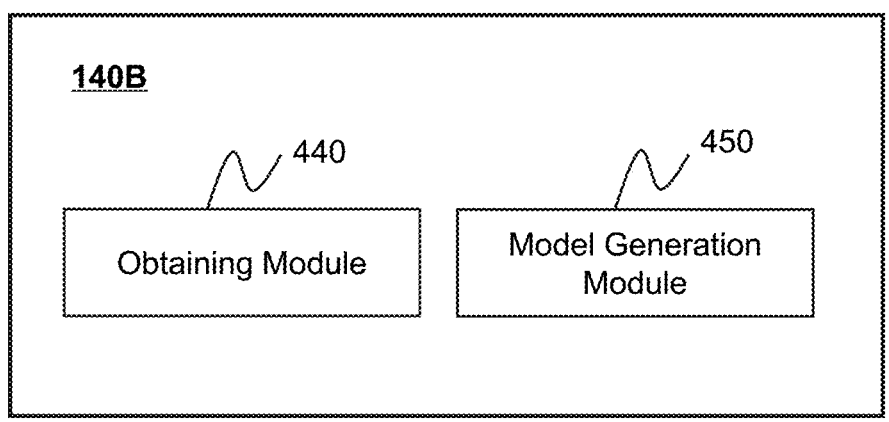

FIGS. 4A and 4B are block diagrams illustrating exemplary processing devices 140A and 140B according to some embodiments of the present disclosure. The processing devices 140A and 140B may be exemplary processing devices 140 as described in connection with FIG. 1. In some embodiments, the processing device 140A may be configured to apply an ROI segmentation model in image segmentation. The processing device 140B may be configured to obtain one or more training samples and/or generate the ROI segmentation model using the training samples. In some embodiments, the processing devices 140A and 140B may be respectively implemented on a processing unit (e.g., a processor 210 illustrated in FIG. 2 or a CPU 340 as illustrated in FIG. 3). Merely by way of example, the processing devices 140A may be implemented on a CPU 340 of a terminal device, and the processing device 140B may be implemented on a computing device 200. Alternatively, the processing devices 140A and 140B may be implemented on a same computing device 200 or a same CPU 340. For example, the processing devices 140A and 140B may be implemented on a same computing device 200.

As shown in FIG. 4A, the processing device 140A may include an obtaining module 410, a segmentation module 420, and a determination module 430.

The obtaining module 410 may be configured to acquire information relating to the imaging system 100. For example, the obtaining module 410 may obtain a target image that includes an ROI to be segmented. More descriptions regarding the obtaining of the target image may be found elsewhere in the present disclosure. See, e.g., operation 510 and relevant descriptions thereof.

The segmentation module 420 may be configured to segment an image. For example, the segmentation module 420 may segment a preliminary region representative of the ROI from the target image using a first ROI segmentation model corresponding to a first image resolution. As another example, the segmentation module 420 may segment a target region representative of the ROI from the preliminary using a second ROI segmentation model corresponding to a second image resolution, wherein the second image resolution may be higher than the first image resolution. In some embodiments, the segmentation module 420 may preprocess (e.g., resample, normalize) an image and segment the preprocessed the image. More descriptions regarding the image segmentation and/or the image preprocessing may be found elsewhere in the present disclosure. See, e.g., operations 520 and 530 and relevant descriptions thereof.

The determination module 430 may be configured to determine a parameter value indicative of a physiological condition of the ROI based on the target region. Based on the parameter value, the determination module 430 may further evaluate the physiological condition of the ROI. For example, the determination module 430 may evaluate the functionality of a polycystic kidney based on the total kidney volume (TKV) of the polycystic kidney and optionally a classification chart regarding polycystic kidney disease. More descriptions regarding the determination of the parameter value and the evaluation the physiological condition of the ROI may be found elsewhere in the present disclosure. See, e.g., operations 540 and 550 and relevant descriptions thereof.

As shown in FIG. 4B, the processing device 140B may include an obtaining module 440 and a model generation module 450.

The obtaining module 440 may be configured to obtain at least one training image and a preliminary model. The training image may refer to an image of a sample object that has a known ROI (which is annotated in the image). Each of the at least one training image may have a target image resolution and include an annotated ROI in the training image. The preliminary model may be any type of neural network model that is to be trained as an ROI segmentation model corresponding to the target image resolution (e.g., a first ROI segmentation model corresponding to a first image resolution or a second ROI segmentation model corresponding to a second image resolution as described elsewhere in this disclosure).

The model generation module 450 may be configured to generate the ROI segmentation model corresponding to the target image resolution by training the preliminary model using the at least one training image. For example, the model generation module 450 may train the preliminary model according to a machine learning algorithm. In some embodiments, the model generation module 450 may train the preliminary model by iteratively updating model parameter(s) of the preliminary model. More descriptions regarding the training of the preliminary model may be found elsewhere in the present disclosure. See, e.g., operation 1230 and relevant descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 140A and/or the processing device 140B may share two or more of the modules, and any one of the modules may be divided into two or more units. For instance, the processing devices 140A and 140B may share a same obtaining module; that is, the obtaining module 410 and the obtaining module 440 are a same module. In some embodiments, the processing device 140A and/or the processing device 140B may include one or more additional modules, such a storage module (not shown) for storing data. In some embodiments, the processing device 140A and the processing device 140B may be integrated into one processing device 140.

Figure 5:
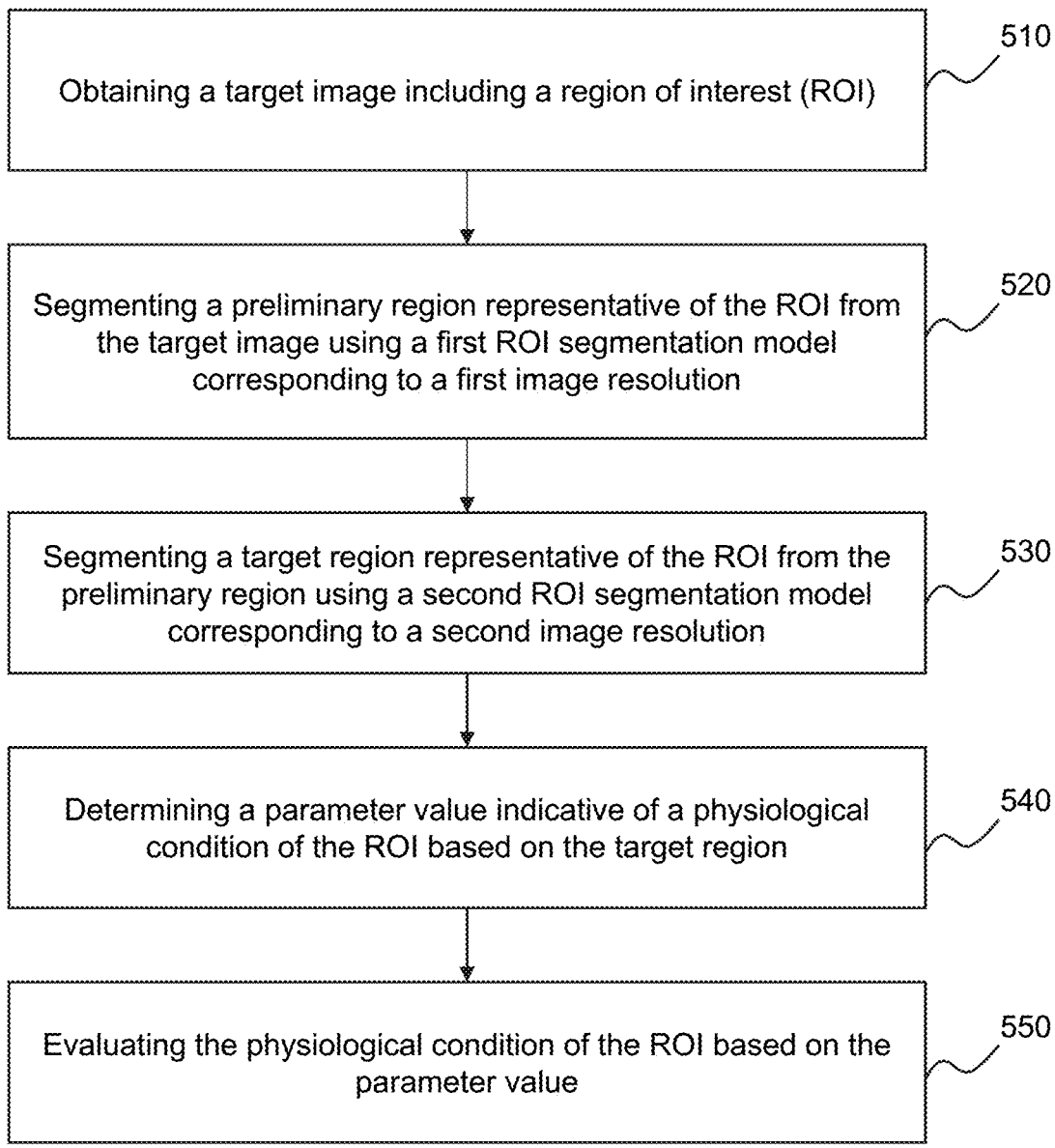
FIG. 5 is a flowchart illustrating an exemplary process for image segmentation according to some embodiments of the present disclosure.

FIG. 5 is a flowchart illustrating an exemplary process for image segmentation according to some embodiments of the present disclosure. In some embodiments, one or more operations of process 500 illustrated in FIG. 5 may be implemented in the imaging system 100 illustrated in FIG. 1. For example, the process 500 may be stored in a storage device (e.g., the storage device 150 and/or the storage 220) of the imaging system 100 in the form of instructions, and invoked and/or executed by the processing device 140A (e.g., the processor 210 of the computing device 400 as illustrated in FIG. 2, the CPU 340 of the mobile device 300 as illustrated in FIG. 3, or one or more modules of the processing device 140A illustrated in FIG. 4A).

In 510, the processing device 140A (e.g., the obtaining module 410) may obtain a target image including an ROI.

As used herein, a target image refers to an image that includes an ROI to be segmented. An ROI of the target image refers to a portion in the target image that represents a physical region of interest of an object. The object may include a biological object and/or a non-biological object. For example, the target image may be an image of a patient, and the ROI of the target image may be a specific organ, a specific tissue, or the whole body of the patient. Merely by way of example, the ROI may include the head, the chest, a lung, the heart, the liver, the spleen, the pleura, the mediastinum, the abdomen, the large intestine, the small intestine, the bladder, the gallbladder, the pelvis, the spine, the skeleton, blood vessels, or the like, or any combination thereof, of a patient. In some embodiments, the ROI may include a left kidney and/or a right kidney of the patient. In some embodiments, the ROI may include a lesion of the object. A lesion refers to a damage (or potential damage) and/or an abnormal change (or potential change) in the tissue of the object, usually caused by disease or trauma. For example, the ROI may include a polycystic kidney of a patient caused by autosomal dominant polycystic kidney disease (ADPKD).

In some embodiments, the target image may be a one-dimensional image, a 2D image (e.g., a slice image), a 3D image, a 4D image (e.g., a series of 3D images over time), and/or any related image data (e.g., scan data, projection data), or the like. In some embodiments, the target image may include a medical image generated by a biomedical imaging technique as described elsewhere in this disclosure. For example, the target image may include a CT image, an MRI image, an X-ray image, a PET image, an OCT image, a US image, an IVUS image, a NIRS image, etc. In some embodiments, the target image may be an MRI image including a polycystic kidney of a patient.

In some embodiments, the processing device 140A may obtain the target image from one or more components of the imaging system 100. For example, the processing device 140A may obtain the target image from the imaging device 110. As another example, the processing device 140A may obtain the target image from a storage device (e.g., the storage device 150, the storage 220, or the storage 390) of the imaging system 100 via a network (e.g., the network 120). Alternatively, the processing device 140A may obtain the target image from an external source (e.g., a medical database) via a network (e.g., the network 120).

In 520, the processing device 140A (e.g., the segmentation module 420) may segment a preliminary region representative of the ROI from the target image using a first ROI segmentation model corresponding to a first image resolution.

In 530, the processing device 140A may segment a target region representative of the ROI from the preliminary using a second ROI segmentation model corresponding to a second image resolution. The second image resolution may be higher than the first image resolution.

The preliminary region refers to a region representative of the ROI which is roughly or coarsely segmented from the target image. The target region refers to a region representative of the ROI refined from the preliminary region. For example, the preliminary region may be represented by a bounding box enclosing the ROI. The bounding box may have the shape of a square, a rectangle, a triangle, a polygon, a circle, an ellipse, an irregular shape, or the like. The target region may be a region where the ROI locates refined from the bounding box. Merely by way of example, the target image may be an image of the thorax of a patient and the ROI may be the liver of the patient. The preliminary region may be represented by a rectangular bounding box enclosing the liver, and the target region may be a region representative of the liver within the rectangular bounding box.

As used herein, an ROI segmentation model corresponding to a certain image solution refers to a neural network model configured to receive an image having the certain image resolution and segment the ROI from the image. The ROI segmented by the ROI segmentation model corresponding to the certain image resolution may have the certain image resolution. In some embodiments, the image resolution of an image may be measured by a size of the pixels or voxels of the image. The larger the size of the pixels or voxels of the image is, the lower image resolution the image may have. The first image resolution of the first ROI segmentation model may be lower than the second image resolution of the second ROI segmentation model as aforementioned. Merely by way of example, the first image resolution may be [6 mm, 6 mm, 6 mm], and the second image resolution may be [1 mm, 1 mm, 1 mm].

In some embodiments, an ROI segmentation model (e.g., anyone of the first and second ROI segmentation models) may be obtained from one or more components of the imaging system 100 or an external source via a network (e.g., the network 120). For example, the ROI segmentation model may be previously trained by a computing device (e.g., the processing device 140B), and stored in a storage device (e.g., the storage device 150, the storage 220, and/or the storage 390) of the imaging system 100. The processing device 140A may access the storage device and retrieve the ROI segmentation model. In some embodiments, the ROI segmentation model may be generated according to a machine learning algorithm. The machine learning algorithm may include but not be limited to an artificial neural network algorithm, a deep learning algorithm, a decision tree algorithm, an association rule algorithm, an inductive logic programming algorithm, a support vector machine algorithm, a clustering algorithm, a Bayesian network algorithm, a reinforcement learning algorithm, a representation learning algorithm, a similarity and metric learning algorithm, a sparse dictionary learning algorithm, a genetic algorithm, a rule-based machine learning algorithm, or the like, or any combination thereof. The machine learning algorithm used to generate the ROI segmentation model may be a supervised learning algorithm, a semi-supervised learning algorithm, an unsupervised learning algorithm, or the like. In some embodiments, the ROI segmentation model may be generated by a computing device (e.g., the processing device 140B) by performing a process (e.g., process 1200) for generating an ROI segmentation model disclosed herein. More descriptions regarding the generation of the ROI segmentation model may be found elsewhere in the present disclosure. See, e.g., FIG. 12 and relevant descriptions thereof.

The first and second ROI segmentation models may be of a same type model or different types of models. In some embodiments, at least one model of the first and second ROI segmentation models may be a convolutional neural network (CNN) model, such as a V-net model, a U-net model, an AlexNet model, an Oxford Visual Geometry Group (VGG) model, a ResNet model, or the like, or any combination thereof. In some embodiments, at least one model of the first and second ROI segmentation models may include an input layer, a convolutional layer, a batch normalization layer, an activation layer, an output layer, or the like, or any combination thereof.

In some embodiments, at least one of the first and second ROI segmentation model may include a plurality of convolutional layers. At least one of the convolutional layers may have a count of input channels different from its count of output channels. As used herein, a count of input channels of a convolutional layer may be equal to a count of feature maps inputted into and need to be processed by the convolutional layer. A count of output channels of a convolutional layer may be equal to a count of feature maps outputted by the convolutional layer (i.e., a count of kernels that the convolutional layer has). Optionally, the convolutional layers of the at least one model may form a Bottleneck structure. For example, the Bottleneck structure may include a first convolutional layer and a second convolutional layer downstream to the first convolutional layer. In some embodiments, the second convolutional layer may be adjacent to the first convolutional layer in the at least one model. As used herein, if there is no convolutional layer present between the first and second convolutional layers in the at least one model, the first and second convolutional layers may be regarded as being adjacent to each other. Alternatively, the second convolutional layer may not be adjacent to the first convolutional layer, and one or more middle convolutional layers may present between the first and second convolutional layers. In some embodiments, the second convolutional layer may be directly connected to and immediately follow the first convolutional layer (i.e., no intervening layers are present between the first and second convolutional layers), or indirectly connected to the first convolutional layer (i.e., one or more other layers, such as a batch normalization layer, an activation layer, are present between the first and second convolutional layers). A count of output channels of the first convolutional layer may be smaller than a count of input channels of the first convolutional layer. A count of output channels of the second convolutional layer may be greater than a count of input channels of the second convolutional layer. The channels of the Bottleneck structure may be reduced at the first convolutional layer and increased at the second convolutional layer. Optionally, the Bottleneck structure may further include one or more third convolutional layers between the first and second convolutional layers. The count of input channels of each third convolutional layer may be equal to the count of output channels of the third convolutional layer. More descriptions regarding the configuration of the at least one model may be found elsewhere in the present disclosure. See, FIGS. 7-11B and relevant descriptions.

In some embodiments, the processing device 140A may input the target image into the first ROI segmentation model, and segment the preliminary region based on an output of the first ROI segmentation model. Optionally, the processing device 140A may preprocess (e.g., normalize and/or resample) the target image, and input the preprocessed target image into the first ROI segmentation model. Merely by way of example, the processing device 140A may perform operations 610 to 630 of process 600 as described in connection with FIG. 6 to segment the preliminary region. In some embodiments, the processing device 140A may input the preliminary region into the second ROI segmentation model, and generate the target region based on an output of the second ROI segmentation model. Optionally, the processing device 140A may preprocess (e.g., normalize and/or resample) the preliminary region, and input the preprocessed preliminary region into the second ROI segmentation model. Merely by way of example, the processing device 140A may perform operations 640 to 660 of process 600 as described in connection with FIG. 6 to segment the target region.

In 540, the processing device 140A (e.g., the determination module 430) may determine a parameter value indicative of a physiological condition of the ROI based on the target region.

Exemplary parameter values of the ROI may include a length, a width, a height, a size, an area, a volume, a location, or the like, of the ROI, or any combination thereof. In some embodiments, the target image may be a 3D image of a patient, and the ROI may include a polycystic kidney of the patient. The processing device 140A may determine a total kidney volume (TKV) of the polycystic kidney based on the target region representative of the polycystic kidney. For example, the TKV may be determined by multiplying a total count of voxels within the target region with a size of the voxels (i.e., the image resolution of the target region).

In 550, the processing device 140A (e.g., the determination module 430) may evaluate the physiological condition of the ROI based on the parameter value.

For example, the processing device 140A may determine the physiological condition by comparing the parameter value with a parameter threshold. If the parameter value is greater than the parameter threshold, the processing device 140A may determine that the physiological condition is abnormal. As another example, the processing device 140A may determine the physiological condition based on a classification chart. The classification chart may be used to classify the physiological condition into one or more classes based on the parameter value of the ROI and optionally other information (e.g., the weight, the height, age, a medical history, etc.) relating to the ROI.

Figure 16:
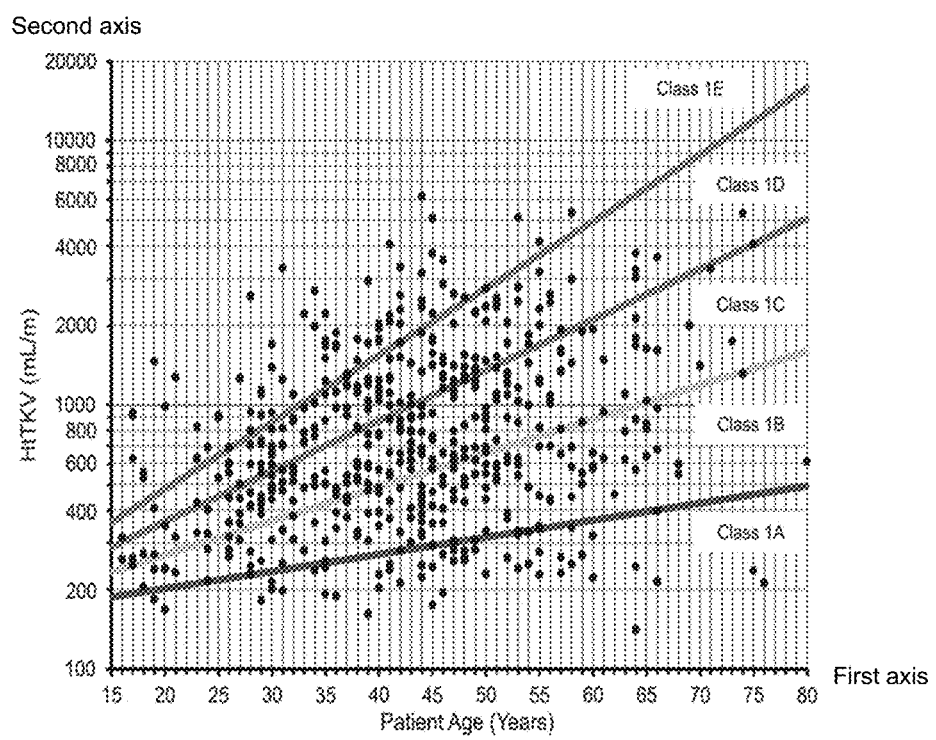
FIG. 16 is a schematic diagram illustrating an exemplary classification chart regarding polycystic kidney disease according to some embodiments of the present disclosure.

For illustration purposes, the following descriptions are described with reference to the determination of the functionality of a polycystic kidney based on the TKV of the polycystic kidney and a classification chart regarding polycystic kidney disease, and not intended to limit the scope of the present disclosure. FIG. 16 illustrates an exemplary classification chart 1600 regarding polycystic kidney disease according to some embodiments of the present disclosure. The classification chart 1600 may include a first axis and a second axis. The first axis may represent a patient age of a patient, and the second axis may represent a ratio (denoted as HtTKV) of the TKV of the patient to the height of the patient. The region defined by the first axis and the second axis may be divided into five sub-regions, each of which may correspond to classes 1A, 1B, 1C, 1D, and 1E, respectively. The classes 1A to 1E may indicate different levels of disease severity and different likelihoods of progression. For a polycystic kidney of a certain patient, the corresponding TKV may be determined by performing operations 510 to 540 as aforementioned. The processing device 140A may further determine the HtTKV of the certain patient based on the determined TKV and the height of the certain patient. The processing device 140A may then determine a sub-region at which a data point corresponding to the certain patient is located based on the HtTKV and the age of the certain patient, and accordingly determine the class of the polycystic kidney.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. The operations of the illustrated process 500 are intended to be illustrative. In some embodiments, the process 500 may be accomplished with one or more additional operations not described, and/or without one or more of the operations discussed. For example, the first ROI segmentation model and the second ROI segmentation model may be integrated into a compound model, which may be used to perform functions of the first ROI segmentation model and the second segmentation model. Operations 510 to 530 may be integrated into a single operation, in which the processing device 140A may segment the target region from the target image by application of the compound model. As another example, operations 510 and 520 may be omitted. The processing device 140A may directly segment the target region from the target region by application of the second ROI segmentation model. As yet another example, the processing device 140A may transmit the physiological condition of the ROI to a terminal (e.g., a terminal 130 of a doctor) for presentation. Additionally, the order in which the operations of the process 500 as illustrated in FIG. 5 and described above is not intended to be limiting.

Figure 6:
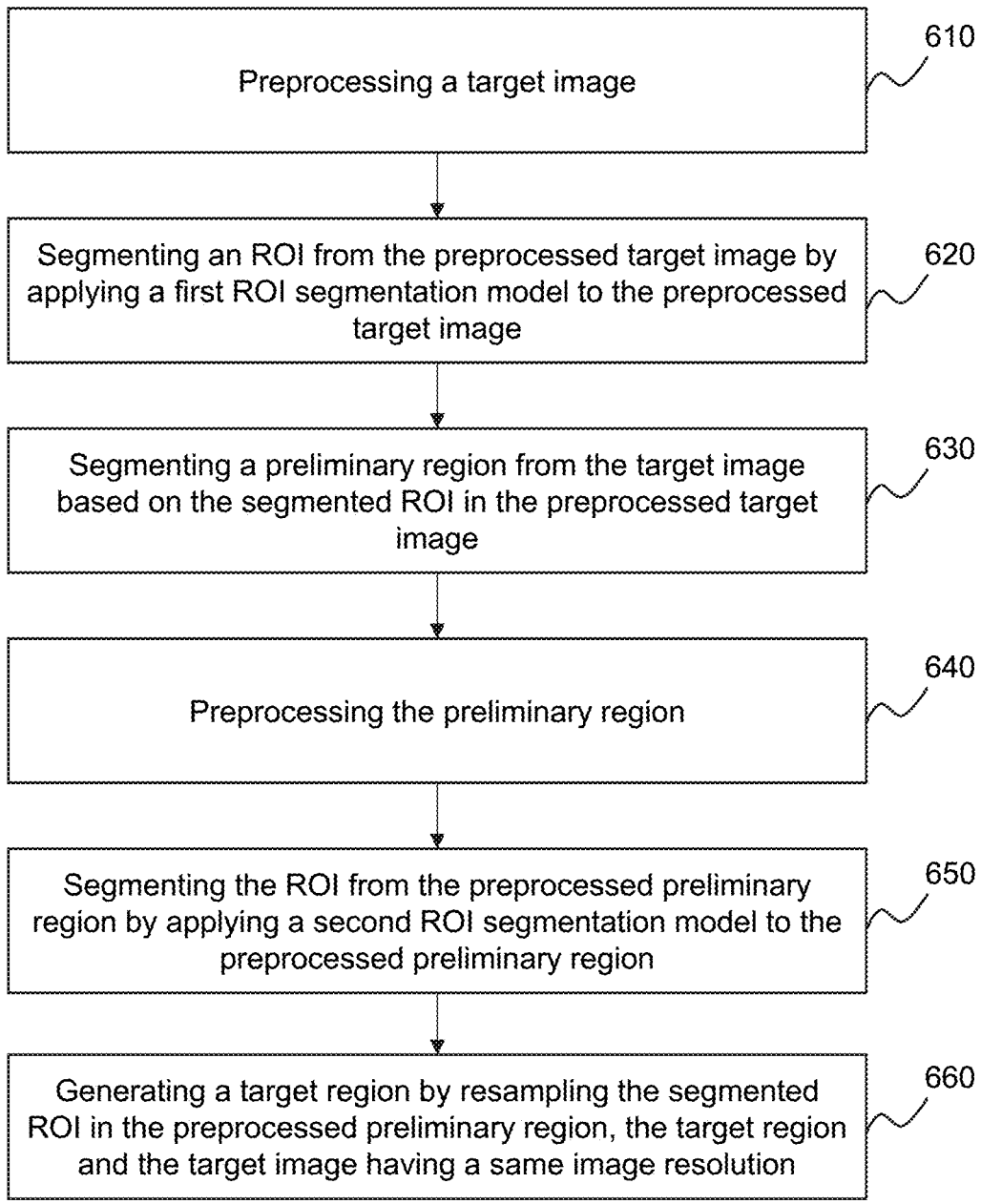
FIG. 6 is a flowchart illustrating an exemplary process for determining a target region representative of an ROI according to some embodiments of the present disclosure.

FIG. 6 is a flowchart illustrating an exemplary process for determining a target region representative of an ROI according to some embodiments of the present disclosure. In some embodiments, one or more operations of the process 600 illustrated in FIG. 6 may be implemented in the imaging system 100 illustrated in FIG. 1. For example, the process 600 may be stored in a storage device (e.g., the storage device 150, and/or the storage 220) of the imaging system 100 in the form of instructions, and invoked and/or executed by the processing device 140A (e.g., the processor 210 of the computing device 200 as illustrated in FIG. 2, the CPU 340 of the mobile device 300 as illustrated in FIG. 3, or one or more modules of the processing device 140A illustrated in FIG. 4). In some embodiments, one or more operations of the process 600 may be performed to achieve at least part of operations 520 and 530 as described in connection with FIG. 5.

In 610, the processing device 140A (e.g., the segmentation module 420) may preprocess the target image.

The preprocessing of the target image may include an image denoising, an image enhancement, an image smoothing, an image transformation, an image resampling, an image normalization, or the like, or a combination thereof. In some embodiments, the preprocessing of the target image may include an image resampling and an image normalization, which may be performed simultaneously or in any sequence. Merely by way of example, the target image may have an image resolution different from the first image resolution of the first ROI segmentation model. The processing device 140A may resample (i.e., resize) the target image to generate a resampled target image having the first image resolution (e.g., [6 mm, 6 mm, 6 mm], [5 mm, 5 mm, 5 mm], [3 mm, 3 mm, 3 mm], etc.). The image resampling of the target image may be performed according to an image resampling algorithm, such as an image interpolation algorithm, a bilinear and bicubic algorithm, a Sinc and Lanczos resampling algorithm, a box sampling algorithm, a mipmap algorithm, a Fourier-transform algorithm, an edge-directed interpolation algorithm, a vectorization algorithm, a deep convolution neural network, or the like, or any combination thereof.

The processing device 140A may further generate the preprocessed target image by normalizing the resampled target image. In some embodiments, the resampled target image may be normalized such that pixel (or voxel) values of the target image may be within a preset range (e.g., [−1, 1]). The normalization operation may be performed using, for example, a linear normalization algorithm, a logarithmic normalization algorithm, an inverse cotangent normalization algorithm, a Z-score standardization normalization algorithm, etc. Merely by way of example, the processing device 140A may range the pixels of the resampled target image according to their pixel values in, for example, descending order or ascending order. The processing device 140A may further normalize the pixel value(s) of pixel(s) in the last 1% to −1 and the pixel value(s) of pixel(s) in the top 1% to 1. The processing device 140A may determine a mean value and a variance of the remaining pixel(s), and normalize the pixel value(s) of the remaining pixel(s) in a range of (−1, 1) based on the mean value and the variance. It should be noted that the above description of preprocessing of the target image is merely provided for the purposes of illustration, and not intended to limit the scope of the present disclosure. For example, the resampling of the target image may be omitted if the image resolution of the target image is equal to the first image resolution.

In 620, the processing device 140A (e.g., the segmentation module 420) may segment the ROI from the preprocessed target image by applying the first ROI segmentation model to the preprocessed target image.

In some embodiments, the preprocessed target image may be inputted into the first ROI segmentation model, and the first ROI segmentation model may generate a first output. For example, the preprocessed target image may include a plurality of pixels. The first output of the first ROI segmentation model may include a first probability map, which may include a first probability value of each pixel indicative of a probability that the pixel belongs to the ROI. As another example, the first output may include a first classification map, which may include a first classification label of each pixel indicative of a classification (e.g., within the ROI or not) that the pixel belongs. The processing device 140A may segment the ROI from the preprocessed target image based on the first output of the first ROI segmentation model. For example, the processing device 140A may segment a region (e.g., a maximal region of connected pixels) in the preprocessed target image as an ROI in the preprocessed target image. The segmented region may include a plurality of pixels whose first probability values are greater than a threshold value (e.g., 0.8, 0.85, 0.9, or 0.95) or whose first classification labels indicate that they are within the ROI. In some embodiments, the first ROI segmentation model may directly output the segmented ROI in the preprocessed target image in response to the inputted preprocessed target image.

In some embodiments, the ROI may include a plurality of sub-ROIs. Merely by way of example, the ROI may include a left kidney and a right kidney. For each of the plurality of pixels in the target image, the first probability map may include a first probability value corresponding to the left kidney and a first probability value corresponding to the right kidney. The processing device 140A may segment the left kidney based on the first probability values of the pixels corresponding to the left kidney, and the right kidney based on the first probability values of the pixels corresponding to the right kidney. Optionally, the pixels of the left kidney may be assigned with a first label and the pixels of the right kidney may be assigned with a second label.

In 630, the processing device 140A (e.g., the segmentation module 420) may segment the preliminary region from the target image based on the segmented ROI in the preprocessed target image.

In some embodiments, the processing device 140A may determine a region in the target image corresponding the segmented ROI in the preprocessed target image based on, for example, the location, size, and/or area of the segmented ROI in the preprocessed target image. The processing device 140A may further generate a bounding box having a certain shape (e.g., a square, a rectangle, a triangle, an irregular shape) enclosing the determined region to represent the preliminary region.

After the preliminary region representative of the ROI is segmented from the target image, the processing device 140A may further perform operations 640 to 670 to segment the target region representative of the ROI from the preliminary region by application of the second ROI segmentation model.

In 640, the processing device 140A (e.g., the segmentation module 420) may preprocess the preliminary region.

The preprocessing of the preliminary region may include one or more image processing operations as described elsewhere in this disclosure (e.g., 610 and the relevant descriptions). In some embodiments, the preprocessing of the preliminary region may be performed in a similar manner with that of the target image as described in operation 610. For example, the preliminary region may be resampled to generate a resampled preliminary region that has the second image resolution of the second ROI segmentation model. The resampled preliminary region may be further normalized to generate the preprocessed preliminary region.

In 650, the processing device 140A (e.g., the segmentation module 420) may segment the ROI from the preprocessed preliminary region by applying the second ROI segmentation model to the preprocessed preliminary region.

In some embodiments, the segmentation of the ROI from the preprocessed preliminary region by applying the second ROI segmentation model may be performed in a similar manner with the segmentation of the ROI from the preprocessed target image by applying the first ROI segmentation model as described in operation 620. For example, the preprocessed preliminary region may be inputted into the second ROI segmentation model, and the second ROI segmentation model may output a second output, such as a second probability map or a second classification map. The processing device 140A may further segment the ROI from the preprocessed preliminary region based on the second output. As another example, the preprocessed preliminary region may be inputted into the second ROI segmentation model, and the second ROI segmentation model may directly output the segmented ROI in the preprocessed preliminary region.

In 660, the processing device 140A (e.g., the segmentation module 420) may generate the target region by resampling the segmented ROI in the processed preliminary region, wherein the generated target region may have a same resolution as the target image.

In some embodiments, the resampling of the segmented ROI in the preprocessed preliminary region may be performed according to an image resampling algorithm as described elsewhere in this disclosure (e.g., operation 610 and the relevant descriptions). In some embodiments, the processing device 140A may determine a region in the original target image corresponding to the segmented ROI in the preprocessed preliminary region, and designate the determined region as the target region. Optionally, the processing device 140A may perform disease diagnosis on the ROI based on the segmented target region, such as evaluate the physiological condition of the ROI by performing operations 540 and 550.

In some embodiments, by segmenting the preliminary region from the target region using the first ROI segmentation model and subsequently segmenting the target region from the preliminary region using the second ROI segmentation model may improve the efficiency of the process by reducing, e.g., the processing time, the computational complexity and/or cost, etc. For example, the target region segmentation may be performed on the preliminary region, which is relatively smaller than the original target image, thereby costing shorter time and less computational resources.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. The operations of the illustrated process 600 are intended to be illustrative. In some embodiments, the process 600 may be accomplished with one or more additional operations not described, and/or without one or more of the operations discussed. For example, operations 620 to 640 may be omitted, and the target region may be segmented from the processed target image by merely using the second segmentation model. As another example, operations 610 may be omitted, and operation 620 may be performed to segment the ROI from the original target image. As yet another example, operations 640 may be omitted, and operation 650 may be performed to segment the ROI from the original preliminary region. Additionally, the order in which the operations of the process 600 as illustrated in FIG. 6 and described above is not intended to be limiting.

Figure 7:
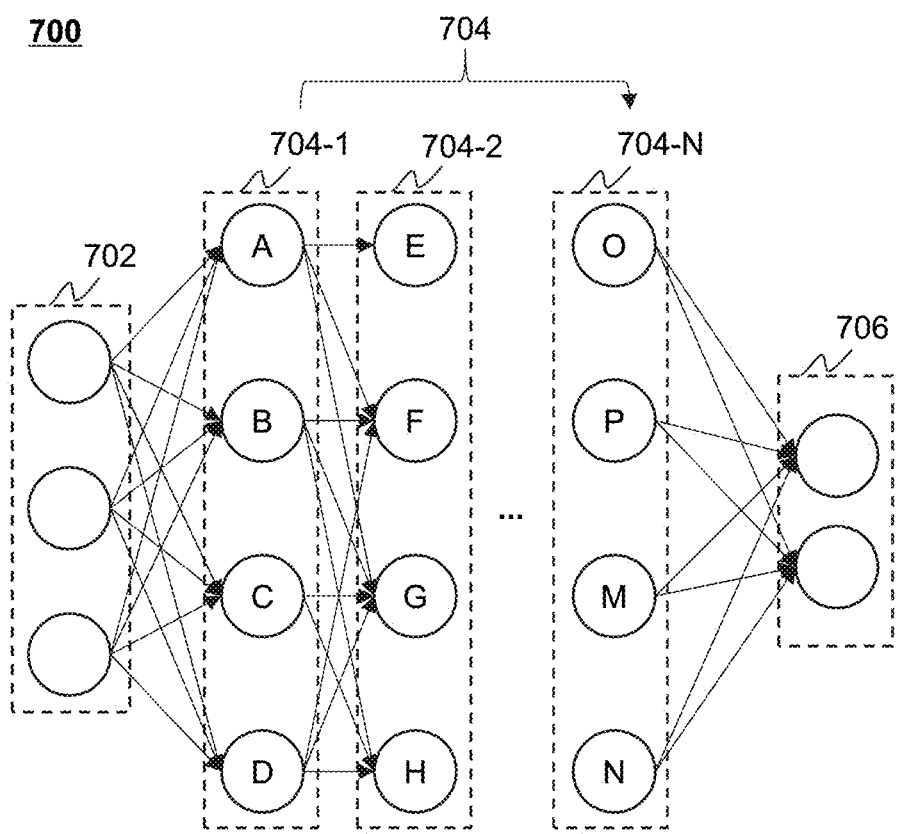
FIG. 7 is a schematic diagram illustrating an exemplary CNN model according to some embodiments of the present disclosure.

FIG. 7 is a schematic diagram illustrating an exemplary CNN model 700 according to some embodiments of the present disclosure. In some embodiments, an ROI segmentation model (e.g., the first ROI segmentation model, the second ROI segmentation model) disclosed herein may have a same configuration as or a similar configuration to the CNN model 700.

As shown in FIG. 7, the CNN model 700 may include an input layer 702, a plurality of hidden layers 704, and an output layer 706. The hidden layers 704 may include a convolutional layer, a rectified linear unit (ReLU) layer, a pooling layer, a fully connected layer, or the like, or any combination thereof. For illustration purposes, exemplary hidden layers 704, including a convolutional layer 704-1, a pooling layer 704-2, and a fully connected layer 704-N, are provided in FIG. 7.

In some embodiments, an image (e.g., a training image, a target image) may be inputted into the input layer 702 of the CNN model 700. The image may be represented as a 2D matrix or a 3D matrix including a plurality of elements (e.g., pixels or voxels). Each of the plurality of elements in the matrix may have a value representing a feature or characteristic of the element. In some embodiments, the inputted image (or referred to as an input tensor) may be represented as $x*y*z*c$, wherein $x*y*z$ may represent the size of the image, and c represents a count of channels of the inputted image (e.g., being equal to 1 for a grey image and 3 for a color image).

The convolutional layer 704-1 may include a plurality of kernels (e.g., A, B, C, and D), which may be used to extract a feature of the image. In some embodiments, each kernel of the plurality of kernels may filter a portion of the image to generate a specific feature corresponding to the portion. The specific feature may be determined based on the kernels. Exemplary features may include a low-level feature (e.g., an edge feature, a textural feature), a high-level feature, or a complicated feature. In some embodiments, features extracted using one kernel may form one feature map corresponding to the kernel, wherein the feature map may be feed into a next layer connected to the convolutional layer 704-1. In some embodiments, the convolutional layer 704-1 may be represented by $x_1*y_1*z_1*c_1*c_2$, wherein $x_1*y_1*z_1$ may represent the size of the kernels in the convolutional layer 704-1, $c_1$ may represent a count of input channels of the convolutional layer 704-1, and $c_2$ may represent a count of output channels of the convolutional layer 704-1.

Figure 9:
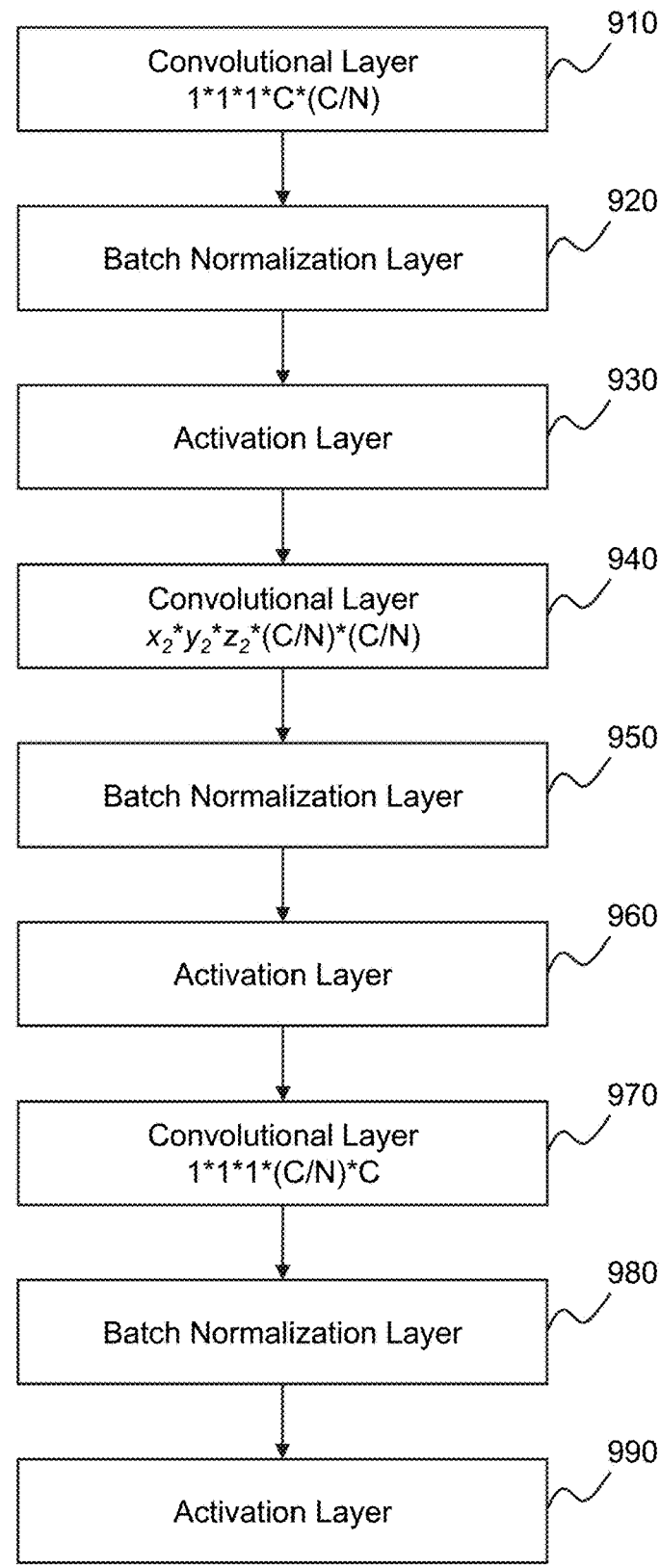
FIG. 9 is a schematic diagram illustrating an exemplary Bottleneck structure according to some embodiments of the present disclosure.

In some embodiments, the count of input channels of the convolutional layer 704-1 may be equal to the count of output channels of the convolutional layer 704-1. In order to reduce the memory space needed for storing the CNN model 700, the convolutional layer 704-1 may be replaced by a Bottleneck structure according to some embodiments of the present disclosure. The Bottleneck structure may include a plurality of convolutional layers (e.g., convolutional layers as illustrated in FIG. 9). The count of input channels of the at least one convolutional layer of the Bottleneck structure may be different from the count of output channels of the at least one convolutional layer. More descriptions regarding the Bottleneck structure may be found elsewhere in the present disclosure. See, e.g., FIG. 9 and relevant descriptions thereof.

The pooling layer 704-2 may take an output of the convolutional layer 704-1 as an input. The pooling layer 704-2 may include a plurality of pooling nodes (e.g., E, F, G, and H), which may be used to sample the output of the convolutional layer 704-1, so as to reduce the computational load of data processing and accelerate the speed of data processing speed. In some embodiments, a size of the matrix representing the image may be reduced in the pooling layer 704-2.

The fully connected layer 704-N may include a plurality of neurons (e.g., O, P, M, and N). The neurons may be connected to the pooling nodes in the pooling layer 704-2. In the fully connected layer 704-N, a plurality of vectors corresponding to the plurality of pooling nodes may be determined based on one or more features of the image, and a plurality of weighting coefficients may be assigned to the plurality of vectors.

The output layer 706 may determine an output based on the vectors and the weighting coefficients obtained from the fully connected layer 704-N. In some embodiments, an output of the output layer 706 may include a probability map as described elsewhere in this disclosure (e.g., FIG. 6 and the relevant descriptions).

Figure 8:
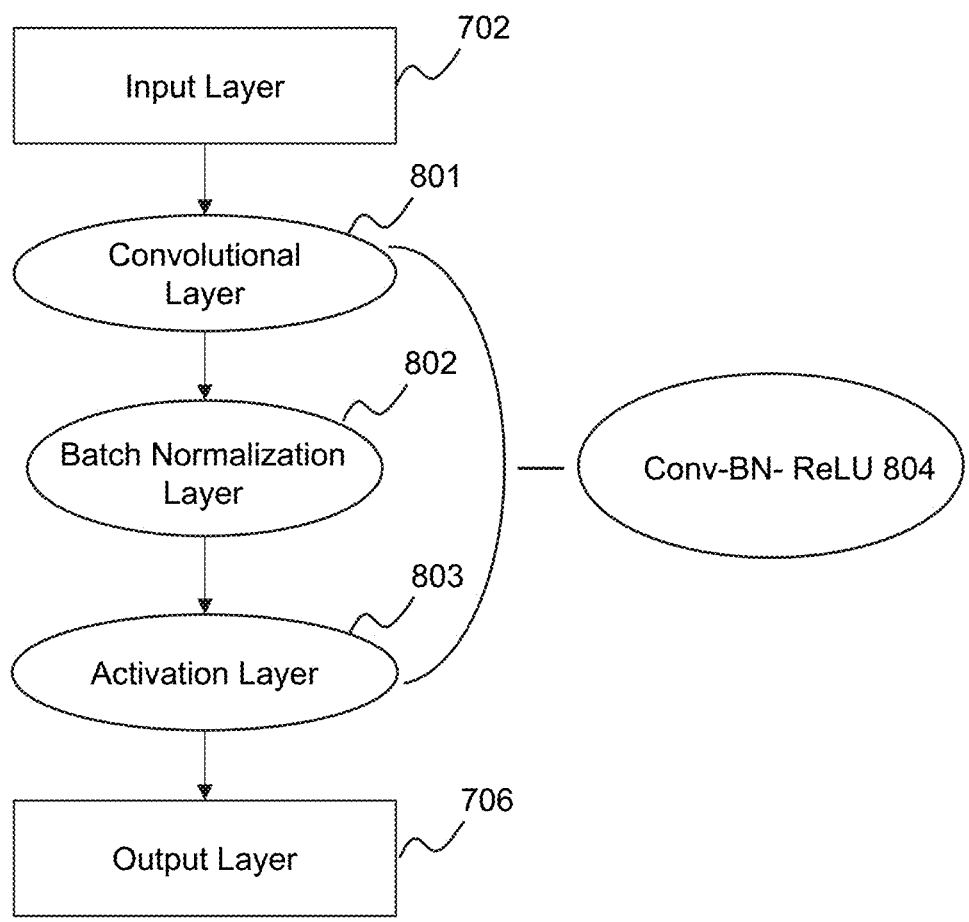
FIG. 8 is a schematic diagram illustrating another exemplary CNN model according to some embodiments of the present disclosure.

FIG. 8 is a schematic diagram illustrating an exemplary CNN model 800 according to some embodiments of the present disclosure. The CNN model 800 may be similar to the CNN model 700 as described in connection with FIG. 7, except that the CNN model 800 may include a Conv-BN-ReLU structure 804.

As shown in FIG. 8, the Conv-BN-ReLU structure 804 may include a convolutional layer 801, a batch normalization layer 802, and an activation layer 803. The batch normalization layer 802 may be configured to receive and normalize an output of the convolutional layer 801 (e.g., feature maps). The data normalization performed by the batch normalization layer 802 may accelerate the convergence of the CNN model 800 and improve the stability of the CNN model 800. The activation layer 803 may include an activation function that is configured to perform a nonlinear transformation on an input received from the batch normalization layer 802. Exemplary activation functions a rectified linear unit (ReLU) function, a sigmoid function, a tan h function, a maxout function, or the like. In some embodiments, the Conv-BN-ReLU structure 804 may be replaced by a Bottleneck structure as described elsewhere in this disclosure (e.g., FIG. 9 and the relevant descriptions).

In some embodiments, the CNN model 700 and/or the CNN model 800 may be implemented on one or more processing devices (e.g., the processing device 140, the processor 210 of the computing device 200). Taking the CNN model 700 for example, a plurality of processing devices may execute a parallel processing operation in some layers of the CNN model 700 by, for example, assigning two or more processing devices for an operation of different nodes (e.g., a kernel, a pooling node, a neuron) in the CNN model 700. For example, a first GPU may execute the operation corresponding to the kernel A and kernel B, and a second kernel may execute the operation corresponding to the kernel C and kernel D. Similarly, a plurality of GPUs may also execute the operation of other nodes (e.g., a kernel, a pooling node, a neuron) in the CNN model 700. In addition, in some embodiments, a storage device (e.g., the storage device 150, the storage 220 of the computing device 200) may be provided for storing data related to the CNN model 700, such as activations and learned weights for each node.

It should be noted that the examples in FIGS. 7 and 8 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the CNN model 700 and/or the CNN model 800 may include one or more additional components. Additionally or alternatively, one or more components of the CNN model 700 and/or the CNN model 800 described above may be omitted. As another example, the CNN model 700 and/or the CNN model 800 may include any number of layers and nodes.

FIG. 9 is a schematic diagram illustrating an exemplary Bottleneck structure 900 according to some embodiments of the present disclosure. In some embodiments, the Bottleneck structure 900 may be a portion of a CNN model as described elsewhere in this disclosure (e.g., FIGS. 7 and 8 and the relevant descriptions). For example, the Bottleneck structure 900 may replace the Conv-BN-ReLU structure 804 of the CNN model 800.

As shown in FIG. 9, the Bottleneck structure 900 may include a plurality of sequentially connected layers including a convolutional layer 910, a batch normalization layer 920, an activation layer 930, a convolutional layer 940, a batch normalization layer 950, an activation layer 960, a convolutional layer 970, a batch normalization layer 980, and an activation layer 990. The output of the convolutional layer 910 may be processed by the batch normalization layer 920 and the activation layer 930, and feed into the convolutional layer 940. The output of the convolutional layer 940 may be processed by the batch normalization layer 950 and the activation layer 960, and feed into the convolutional layer 970. The output of the convolutional layer 970 may be processed by the batch normalization layer 980 and the activation layer 990, and outputted to another layer of the CNN (e.g., an output layer).

The convolutional layer 910 may apply one or more 1*1*1 kernels to its input. The count of input channels of the convolutional layer 910 may be larger than the count of output channels of the convolutional layer 910 such that the convolutional layer 910 may be configured to reduce the channels (or dimensions) of the Bottleneck structure 900. Merely by way of example, the count of input channels and the count of output channels of the convolutional layer 910 may be equal to C and C/N, respectively, wherein N may be equal to any positive integer, such as 2, 3, 4, 5, etc. N may be also referred to as a dimension reduction coefficient of the convolutional layer 910.

The convolutional layer 940 may include one or more kernels each of which has a size of $x_2*y_2*z_2$. The $x_2$, $y_2$, and $z_2$ may be any positive integer, which may be equal to, or partially or completely different from each other. The count of input channels of the convolutional layer 940 may be equal to the count of output channels of the convolutional layers 940. Merely by way of example, the count of input channels and the count of output channels of the convolutional layer 940 may be both equal to C/N.

The convolutional layer 970 may apply one or more 1*1*1 kernels to its input. The count of the input channels of the convolutional layer 970 may be less than the count of output channels of the convolutional layer 970 such that the convolutional layer 970 may be configured to increase the channels (or dimensions) of the Bottleneck structure 900. Merely by way of example, the count of input channels and the count of output channels of the convolutional layer 970 may be equal to C/N and C, respectively, wherein N may be also referred to as a dimension increment coefficient of the convolutional layer 970.

In some embodiments, the count of input channels of the convolutional layer 910 and the count of the output channels of the convolutional layer 970 may both equal C as aforementioned. Merely by way of example, the convolutional layer 910 may have 256 input channels, and N may be equal to 4. The convolutional layer 910 may be represented as 1*1*1*256*64. The convolutional layer 940 may be represented as 3*3*3*64*64. The convolutional layer 970 may be represented as 1*1*1*64*256. In such cases, the channels of the Bottleneck structure 900 may be reduced by the convolutional layer 910 and changed back to the original value by the convolutional layer 970. In some other embodiments, the count of input channels of the convolutional layer 910 may be different from the count of the output channels of the convolutional layer 970.

In some embodiments, a component of a CNN model (e.g., the convolutional layer 740-1, the Conv-BN-ReLU structure 804) may be replaced by the Bottleneck structure 900 in order to reduce the total count of parameters and/or the required storage space of the CNN model. Merely by way of example, the convolutional layer 801 of the CNN model 800 may have a kernel size K*K*K, C input channels, and C output channels. The count of parameters of the convolutional layer 801 may be equal to $K^3C^2$. If the kernel size of the convolutional layer 940 is equal to K*K*K, the count of parameters of the convolutional layers 910, 940, and 970 may be determined according to Equation (1) as below:

$$1*1*1*C*\frac{C}{N} + K*K*K*\frac{C}{N}*\frac{C}{N} + 1*1*1*\frac{C}{N}*C = \left(\frac{2}{N} + \frac{K^3}{N^2}\right)*C^2.$$ Equation (1)

Thus, using the Bottleneck structure 900 to replace the Conv-BN-ReLU structure 804 may reduce the total count of parameters of the CNN model. Merely by way of example, it is assumed that K is equal to 3. If N is equal to 2, the count of parameters of the convolutional layer 801 may be 3.48 times of that of the convolutional layers 910, 940, and 970. If N is equal to 4, the count of parameters of the convolutional layer 801 may be 12.34 times of that of the convolutional layers 910, 940, and 970. If N is equal to 8, the count of parameters of the convolutional layer 801 may be 40.19 times of that of the convolutional layers 910, 940, and 970. Additionally or alternatively, using the Bottleneck structure 900 to replace the Conv-BN-ReLU structure 804 may reduce the required storage space of the CNN model 800. For example, if N is equal to 4, the required storage space of the CNN model 800 may be reduced more than 30 times from 250 MB to 8.8 MB.

It should be noted that the example in FIG. 9 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the Bottleneck structure 900 may include one or more additional components. For example, the Bottleneck structure 900 may include a plurality of convolutional layers 940 between the convolutional layers 910 and 970. Additionally or alternatively, one or more components of the Bottleneck structure 900 (such as one or more of the batch normalization layers, one or more of the activation layers, and/or the convolutional layer 940) described above may be omitted.

In some embodiments, a parameter value of the Bottleneck structure 900 provided above (e.g., the kernel size, the count of input channels, the count of output channels of a certain convolutional layer) may be illustrative and can be modified according to actual needs. Merely by way of example, the dimension reduction coefficient of the convolutional layer 910 may be different from the dimension increment coefficient of the convolutional layer 970. In addition, a parameter value of the Bottleneck structure 900 may be a default setting of the imaging system 100, manually set by a user of the imaging system 100, or determined by the processing device 140. For example, the processing device 140B may determine the value of N based on a desired size of the CNN model.

Figure 10:
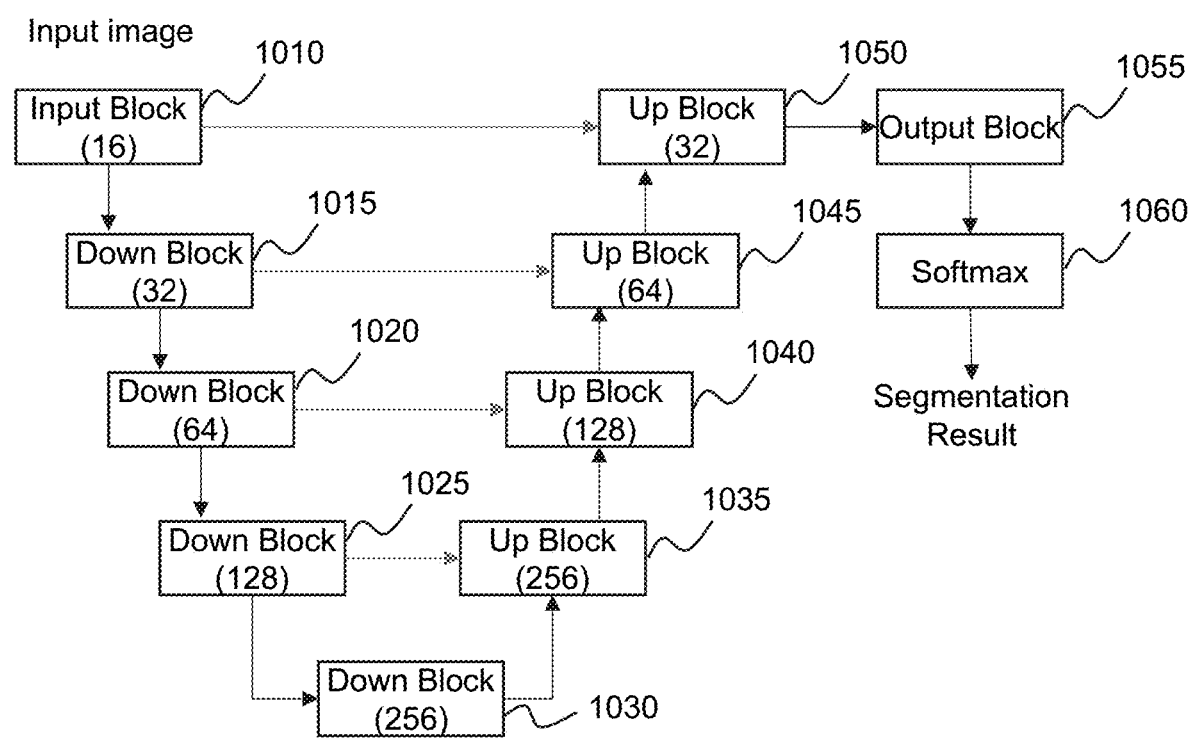
FIG. 10 is a schematic diagram illustrating an exemplary ROI segmentation model according to some embodiments of the present disclosure.

FIG. 10 is a schematic diagram illustrating an exemplary ROI segmentation model 1000 according to some embodiments of the present disclosure. The ROI segmentation model 1000 may be an exemplary embodiment of the first ROI segmentation model and/or the second ROI segmentation model as described in connection with FIGS. 5 and 6. The ROI segmentation model 1000 may be a V-net model incorporated with one or more Bottleneck structures.

As illustrated in FIG. 10, the ROI segmentation model 1000 may include an input block 1010, a plurality of down blocks (e.g., 1015, 1020, 1025, and 1030), a plurality of up blocks (1035, 1040, 1045, and 1050), an output block 1055, and a softmax function 1060. For illustration purposes, an exemplary count of output channels of each of the blocks of the ROI segmentation model 1000 is represented as the number in a bracket in the block as illustrated in FIG. 10. For instance, the count of output channels of the input block 1010 of the ROI segmentation model 1000 may be 16. As another example, the count of output channels of the up block 1050 may be 32.

The input block 1010 may be configured to receive an input image (e.g., a target image as described in connection with FIG. 5, a training image as described in connection with FIG. 12). The down blocks 1015, 1020, 1025, and 1030 may form a compression (or downsampling) path along which the count of output channels may be increased and information (e.g., an output of a specific block) may be downsampled. For example, as shown in FIG. 10, the down block 1015 may receive 16 feature maps with a certain resolution from the input block 1010, process (e.g., downsample and perform a convolution operation on) the 16 feature maps and output 32 feature maps with a lower resolution than the certain resolution (e.g., half of the certain resolution). Similarly, the count of outputted feature maps may be doubled and the resolution of the outputted feature maps may be reduced at each of the down blocks 1020, 1025, and 1030. The ROI segmentation model 1000 may extract features of the input image at different scales (or image resolutions) and have a high image segmentation accuracy.

The up blocks 1035, 1040, 1045, and 1050 may form a decompression (or upsampling) path along which the count of output channels may be decreased and information (e.g., an output of a specific block) may be upsampled. In some embodiments, each up block may receive a first input from a block immediately upstream to and connected to the up block, and a second input from a block at the same layer as the up block via a skip-connection. Merely by way of example, 256 feature maps outputted by the down block 1030 may be upsampled to 128 feature maps with a relatively higher resolution and inputted into the up block 1035. The up block 1035 may also receive 128 feature maps from the down block 1025 via a skip-connection between the down block 1025 and the up block 1035. The 128 feature maps received from the down block 1025 and the 128 upsampled feature maps may be combined and processed by the up block 1035. The up block 1035 may then generate 256 feature maps and feed the generated feature maps into the up block 1040 for further processing. As another example, the 256 feature maps outputted by the up block 1035 may be processed to generate 64 feature maps, which may be inputted into the up block 1040 in combination with 64 feature maps received from the down block 1020 via a skip-connection between the down block 1020 and the up block 1040. Similarly, the count of outputted feature maps may be reduced and the resolution of the outputted feature maps may be increased at each of the up blocks 1045 and 1050.

The output block 1055 may receive an output from the up block 1050 as an input and output a probability map. The probability map may include one or more probability values of each pixel (or voxel) of the input image, wherein a probability value of the pixel (or voxel) may indicate a probability that the pixel (or voxel) belongs to a certain classification (e.g., a background pixel, a left kidney, a right kidney, etc.) The softmax function 1060 may generate a segmentation result based on the probability map outputted by the output block 1055. For example, the ROI segmentation model 1000 may be used to segment a left kidney from the input image. The softmax function 1060 may segment pixels (or voxels) from the input image, wherein the probability value that each segmented pixel belonging to the left kidney is greater than a threshold value.

Figure 11:
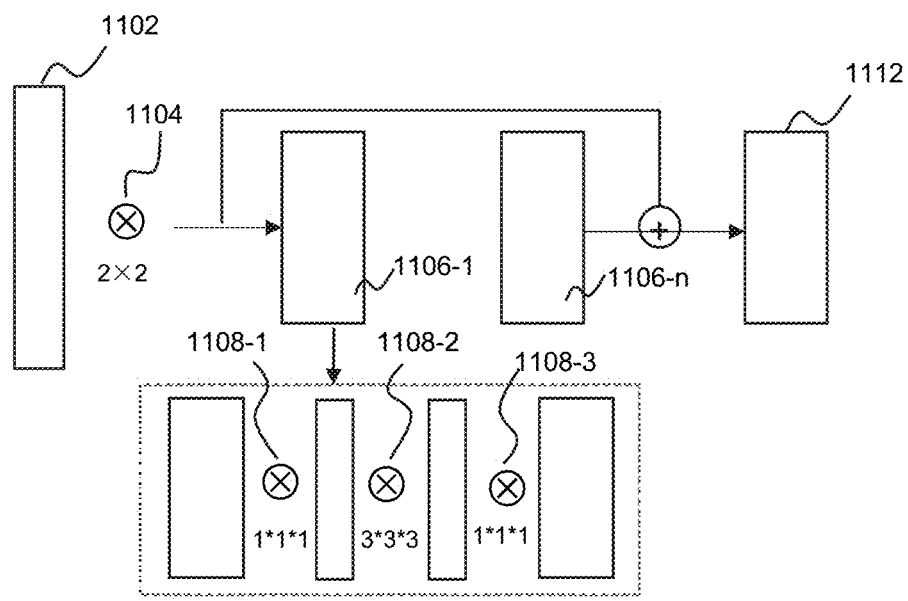
FIG. 11 is a schematic diagram illustrating an exemplary block of an ROI segmentation model according to some embodiments of the present disclosure.

In some embodiments, one or more blocks of the ROI segmentation model 1000 may have a same or similar configuration as a block 1100 with a Bottleneck structure as illustrated in FIG. 11. As illustrated in FIG. 11, the block 1100 may include an input layer 1102, a plurality of convolutional layers (e.g., 1106-1, . . . , and 1106-*n*), and an output layer 1112. The input layer 1102 may be configured to receive feature maps from, e.g., one or more blocks (e.g., a block up immediately upstream to and connected to the block 1100 and/or a block at the same layer as the block 1100).

The feature maps received by the input layer 1102 may be resized by one or more 2*2 kernels 1104 with a stride 2. For example, for a down block of the ROI segmentation model 1000, its 2*2 kernels 1104 may compress the size of the feature maps by half. As another example, for an up block of the ROI segmentation model, its 2*2 kernel 1104 may double the size of the feature maps.

At least one of convolutional layers of the block 1100 may include three sub-convolutional layers that form a Bottleneck structure. For example, as shown in FIG. 11, the convolutional layer 1106-1 may include three sub-convolutional layers 1108-1, 1108-2, and 1108-3. The sub-convolutional layer 1108-1 may be configured to apply one or more 1*1*1 kernels to reduce the channels (or count) of feature maps. The sub-convolutional layer 1108-2 may be configured to apply one or more 3*3*3 kernels on the feature maps outputted by the sub-convolutional layer 1108-1 without changing the channels of feature maps. The sub-convolutional layer 1108-3 may be configured to apply one or more 1*1*1 kernels on the feature maps outputted by the sub-convolutional layer 1108-2 to increase the channels of feature maps. Optionally, the count of the feature maps outputted by the sub-convolutional layer 1108-3 may be equal to the count of the feature maps inputted into the sub-convolutional layer 1108-1.

In some embodiments, the output of the last convolutional layer 1106-*n* may be combined with the input of the convolutional layer 1106-1, and inputted into the output layer 1112.

In some embodiments, a memory utilization strategy may be adopted in the application of the ROI segmentation model 1000. A maximum required memory space may be determined for the blocks of the ROI segmentation model 1000 (or a portion thereof). For example, the up block 1050 may require a maximum memory space among the blocks, and the maximum required memory space may be determined based on the up block 1050. Data relating to the skip connections and data relating to each of the input block 1010, the down blocks 1015 to 1030, and the up blocks 1035 to 1050 may be stored in the maximum required memory space. Merely by way of example, the output of the down block 1030 may be up sampled and stored in a memory space A in the maximum required memory space that is adjacent to a memory space B where the output of the down block 1025 stores in the maximum required memory space. Data stored in the memory space A and the memory space B may serve as input data of the up block 1035. In such cases, there is no need to allocate an additional memory space for storing data relating to the skip connection between the down block 1025 and the up block 1035. Optionally, data relating to the output block 1055 may be stored in an additional memory space other than the maximum required memory space.

It should be noted that the examples illustrated in FIGS. 10 and 11 and the above descriptions thereof are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the ROI segmentation model 1000 may include one or more additional components (e.g., additional down block(s) and/or additional up block(s)). Additionally or alternatively, one or more components of the ROI segmentation model 1000 (e.g., a skip-connection) may be omitted. In addition, a parameter value of the ROI segmentation model 1000 and the block 1100 provided above may be illustrative and can be modified according to actual needs.

Figure 12:
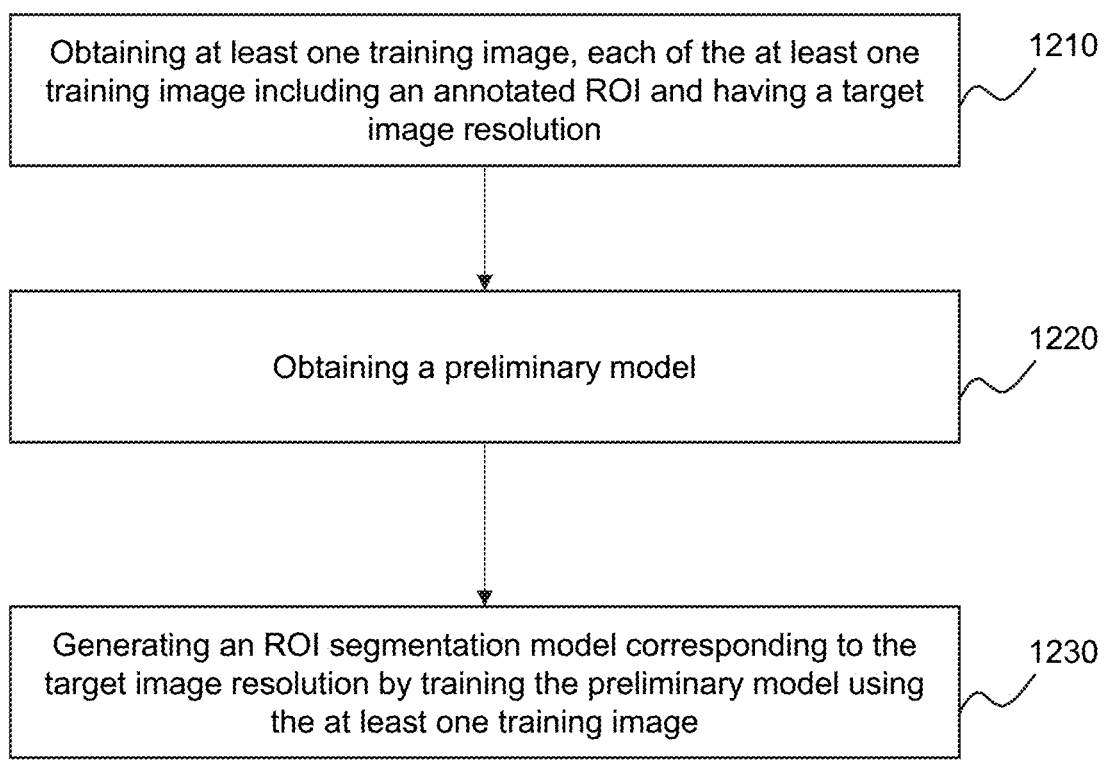
FIG. 12 is a flowchart illustrating an exemplary process for generating an ROI segmentation model corresponding to a target image resolution according to some embodiments of the present disclosure.

FIG. 12 is a flowchart illustrating an exemplary process for generating an ROI segmentation model corresponding to a target image resolution according to some embodiments of the present disclosure. In some embodiments, one or more operations of process 1200 illustrated in FIG. 12 may be implemented in the imaging system 100 illustrated in FIG. 1. For example, the process 1200 may be stored in a storage device (e.g., the storage device 150 and/or the storage 220) of the imaging system 100 in the form of instructions, and invoked and/or executed by the processing device 140B (e.g., the processor 210 of the computing device 400 as illustrated in FIG. 2, the CPU 340 of the mobile device 300 as illustrated in FIG. 3, or one or more modules of the processing device 140B illustrated in FIG. 4B). In some embodiments, the ROI segmentation model may be a first ROI segmentation model or a second ROI segmentation model as described in connection with FIG. 5.

In 1210, the processing device 140B (e.g., the obtaining module 440) may obtain at least one training image. Each of the at least one training image may have the target image resolution and include an annotated ROI in the training image.

A training image refers to an image of a sample object that has a known ROI (which is annotated in the image). In some embodiments, the training image may be of the same type of image as the target image, and the sample object may be of the same type of object as the object in the target image as described in connection with 510. The ROI in the training image may correspond to the same type of physical portion as the ROI in the target image to be segmented. For example, if the ROI segmentation model is used to segment a specific organ (e.g., a left kidney) on a target image of a patient, the training image may be an image of a sample patient, wherein a region representing the specific organ of the sample patient may be annotated in the training image. In some embodiments, a set of images may be annotated with different types of ROIs to generate different sets of training images, wherein the different sets of training images may be used to train different types of ROI segmentation models. For example, a set of chest CT images may be annotated with the heart to generate a set of training images used to train a heart segmentation model, and the set of chest CT images may be annotated with the lung to generate another set of training images used to train a lung segmentation model. In some embodiments, different sets of images may be annotated with different types of ROIs to generate different sets of training images, wherein the different sets of training images may be used to train different types of ROI segmentation models.

In some embodiments, an ROI of a training image may be annotated in any suitable manner. For example, the ROI of the training image may be annotated by assigning a marker or a label to each pixel of the training image. The marker or the label assigned to the pixel may represent, for example, whether the pixel belongs to an ROI of the training image or not, a possibility that the pixel belongs to an ROI of the training image, etc. Merely by way of example, each pixel of the training image may be assigned with "0" or "1," wherein "0" represents that a pixel belongs to a non-ROI of the training image and "1" represents that a pixel belongs to an ROI of the training image. Optionally, the training image may be presented based on the maker or label assigned to each pixel of the training image. For example, the training image may be presented as a binary image, wherein one or more pixels assigned with "0" may be white (or black) and one or more pixels assigned with "1" may be black (or white) in the binary image. In such cases, in the training image, a white area may represent a non-ROI and a black area may represent an ROI.

In some embodiments, a training image may be previously generated and stored in a storage device (e.g., the storage device 150, the storage 220, the storage 390, or an external source). For example, the training image may be a historical image generated using the imaging device 110, wherein an ROI may have been annotated in the historical image by a doctor manually and/or by a computing device automatically. The historical image may be stored in the storage device of the imaging system 100 and retrieved by the processing device 140B from the storage device. Alternatively, the training image may be generated by the processing device 140B. For example, the processing device 140B may process a certain image including an annotated ROI to generate the training image. Merely by way of example, the certain image may have an image resolution different from the target image resolution. The processing device 140B may resample the image to generate a resampled image having the target image resolution. Optionally, the processing device 140B may further normalize the resampled image to generate the training image. As another example, the processing device 140B may extract one or more image crops from the resampled image, and normalize each of the image crop(s) to generate a corresponding training image.

In 1220, the processing device 140B (e.g., the obtaining module 440) may obtain a preliminary model including a plurality of convolutional layers.

In some embodiments, the preliminary model may be any type of neural network model that is to be trained as the ROI segmentation model corresponding to the target image resolution. For example, the preliminary model may include a V-net model, a U-net model, an AlexNet model, an Oxford Visual Geometry Group (VGG) model, a ResNet model, or the like, or any combination thereof. In some embodiments, the preliminary model may include a plurality of convolutional layers. At least one of the plurality of convolutional layers may have a count of input channels different from its a count of output channels. In some embodiments, the convolutional layers (or a portion thereof) of the preliminary model may form a Bottleneck structure as described elsewhere in this disclosure (e.g., FIG. 9 and the relevant descriptions).

In 1230, the processing device 140B (e.g., the model generation module 450) may generate the ROI segmentation model corresponding to the target image resolution by training the preliminary model using the at least one training image.

In some embodiments, the preliminary model to be trained may include one or more model parameters. Exemplary model parameters may include the number (or count) of layers, the number (or count) of nodes, a loss function, or the like, or any combination thereof. Before training, the preliminary model may have one or more initial parameter values of the model parameter(s). In the training of the preliminary model, the value(s) of the model parameter(s) of the preliminary model may be updated.

In some embodiments, the training of the preliminary model may include one or more iterations to iteratively update the model parameters of the preliminary model until a termination condition is satisfied in a certain iteration. Exemplary termination conditions may be that the value of the loss function obtained in the certain iteration is less than a threshold value, that a certain count of iterations have been performed, that the loss function converges such that the difference of the values of the loss function obtained in a previous iteration and the current iteration is within a threshold value, etc. Exemplary loss functions may include a focal loss function, a log loss function, a cross-entropy loss function, a Dice loss function, etc. In some embodiments, the processing device 140B may extract one or more image crops from each of the at least one training image, and train the preliminary model using the extracted image crop(s).

It should be noted that the above description regarding the process 1200 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, one or more operations may be added or omitted. For example, after the ROI segmentation model is generated, the processing device 140B may further test the ROI segmentation model using a set of testing images. Additionally or alternatively, the processing device 140B may update the ROI segmentation model periodically or irregularly based on one or more newly-generated training images (e.g., new annotated images generated in medical diagnosis).

Figure 13A:
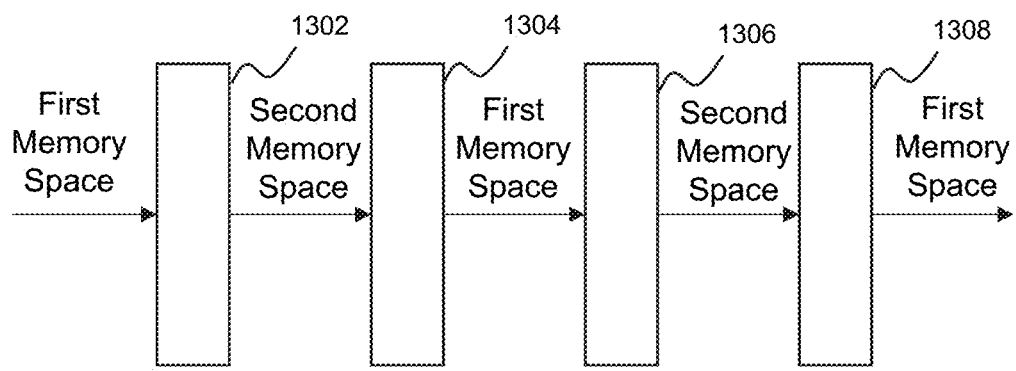
FIGS. 13A and 13B are schematic diagrams illustrating exemplary storage memory utilization strategies used in applying an ROI segmentation model according to some embodiments of the present disclosure.

In some embodiments, during the application of an ROI segmentation model, a memory utilization strategy may be adopted in order to reduce the memory space needed for model application and facilitate the model application. For illustration purposes, a memory utilization strategy used in the application of an ROI segmentation model 1300 illustrated in FIG. 13A is described as an example, and not intended to be limiting.

In some embodiments, the ROI segmentation model 1300 may be loaded in a storage device of the imaging system 100 (e.g., the storage device 150 and/or the storage 220) or an external storage during the application of the ROI segmentation model 1300. As illustrated in FIG. 13A, the ROI segmentation model 1300 may include convolutional layers 1302, 1304, 1306, and 1308. The processing device 140A may determine a first memory space and a second memory space in the storage device based on the convolutional layers of the ROI segmentation model 1300. For example, for each convolutional layer of the ROI segmentation model 1300, the processing device 140A may determine a first size of memory space needed for storing input data of the convolutional layer, and a second size of memory space needed for storing output data of the convolutional layer. The processing device 140A may further determine a first maximum value among the first sizes of the convolutional layers and a second maximum value among the second sizes of the convolutional layers. The first memory space may have a size greater than or equal to the first maximum value, and the second memory space may have a size greater than or equal to the second maximum value. Merely by way of example, the first and second maximum values may both equal to 800 MB, the processing device 140A may determine, in the storage device, a memory space with a size of 800 MB as the first memory space and another memory space with a size of 800 MB as the second memory space.

During the application of the ROI segmentation model 1300, the first memory space and the second memory space may be used interchangeably and repeatedly. For example, the input data and the output data of the convolutional layer 1302 may be stored in the first memory space and the second memory space, respectively. The output data of the convolutional layer 1302 stored in the second memory space may serve as the input data of the convolutional layer 1304. The output data of the convolutional layer 1304 adjacent to the convolutional layer 1302 may be stored in the first memory space. Similarly, the output data of the convolutional layers 1306 and 1308 may be stored on the second memory space and the first memory space, respectively.

Figure 13B:
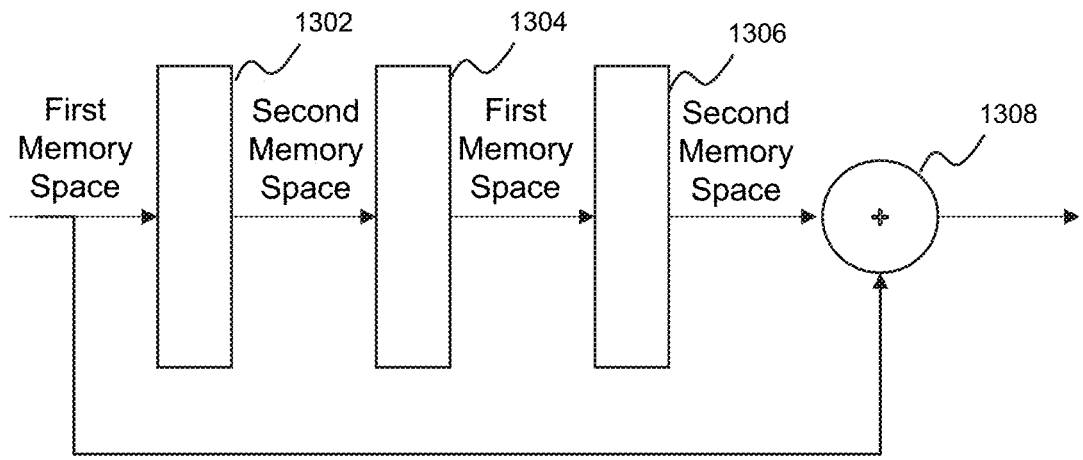

In some embodiments, an additional memory space may be determined by the processing device 140A from the storage device for storing (e.g., temporarily storing) information including, such as an input of the ROI segmentation model 1300, intermediate processing result generated by the ROI segmentation model 1300, one or more algorithms of the ROI segmentation model 1300, etc. Merely by way of example, for an ROI segmentation model 1350 as illustrated in FIG. 13B, an additional memory space may be needed to store the input of the convolutional layer 1302 because the input of the convolutional layer 1302 may need to be combined with the output of the convolutional layer 1306 for further processing. In some embodiments, the ROI segmentation model 1300 or 1350 may be part of a V-net model or a U-net model that includes a skip-connection.

In some embodiments, the convolutional layers 1302 to 1308 or a portion thereof may form a Bottleneck structure as described elsewhere in this disclosure (e.g., FIG. 9 and the relevant descriptions). Merely by way of example, the convolutional layer 1302 may have more input channels than output channels, which may serve as a first convolutional layer of the Bottleneck structure; the convolutional layer 1304 may have the same number of input channels and output channels, which may serve as a third convolutional layer of the Bottleneck structure; and the convolutional layer 1306 may have less input channels than output channels, which may serve as a second convolutional layer of the Bottleneck structure. As another example, the convolutional layers 1302 and 1304 may serve as the first and second convolutional layers of the Bottleneck structure, respectively. In some embodiments, one or more other layers, such as a batch normalization layer and/or an activation layer may present between a pair of adjacent convolutional layers of the ROI segmentation model 1300.

FIGS. 14A to 14I are schematic diagrams illustrating an exemplary process of kidney segmentation according to some embodiments of the present disclosure.

Figure 14A:
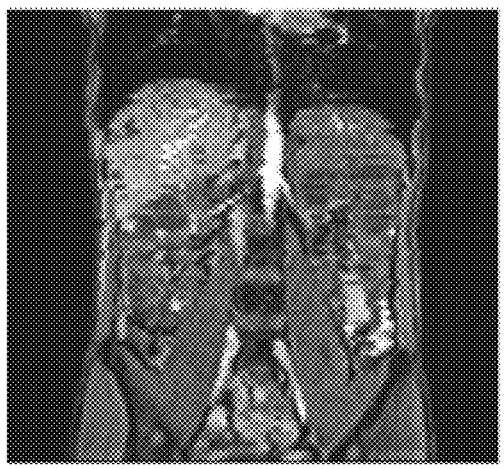
FIGS. 14A to 14I are schematic diagrams illustrating an exemplary process of kidney segmentation according to some embodiments of the present disclosure.

FIG. 14A illustrates an exemplary target image 1400, which includes a right kidney to be segmented and was acquired by a T1 MRI scanner. The size of the target image 1400 is 512*512*90, and the image resolution of the target image 1400 is [1.875 mm, 1.875 mm, 4 mm].

Figure 14B:

FIG. 14B illustrates an exemplary preprocessed target image 1410 generated by preprocessing the target image 1400. The target image 1400 was resampled to generate a resampled target image having a size **80*80*64 and an image resolution [6 mm, 6 mm, 6 mm]. The resampled target image was further normalized to generate the preprocessed target image 1410**.

Figure 14C:
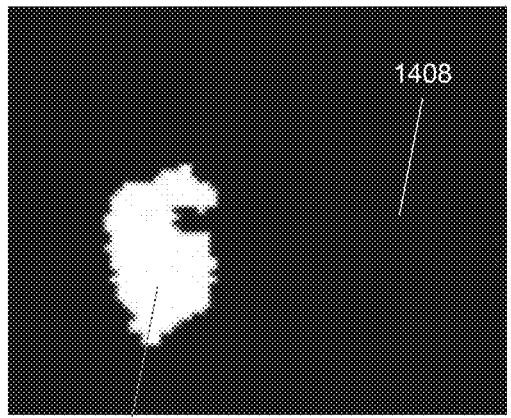

In some embodiments, the image resolution of the preprocessed target image 1410 may be equal to an image resolution of a first ROI segmentation model as described in connection with FIG. 5. The preprocessed target image 1410 was inputted into the first ROI segmentation model to generate a first probability map 1420 of the right kidney as illustrated in FIG. 14C. In the first probability map 1420, probability values of pixels in a white region 1406 may be close to 1, and probability values of pixels in a black region 1408 may be close to 0 (e.g., less than $10^{-6}$). The white region 1406 may be regarded as the right kidney according to the first probability map 1420.

Figure 14D:
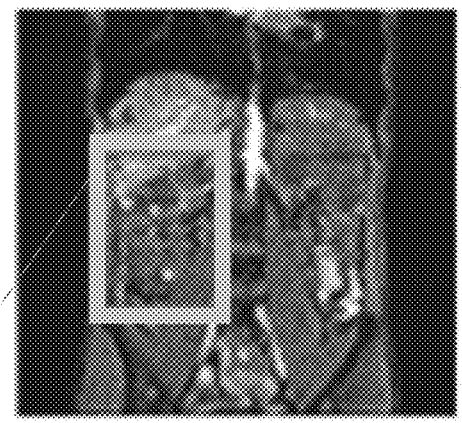
Figure 14E:
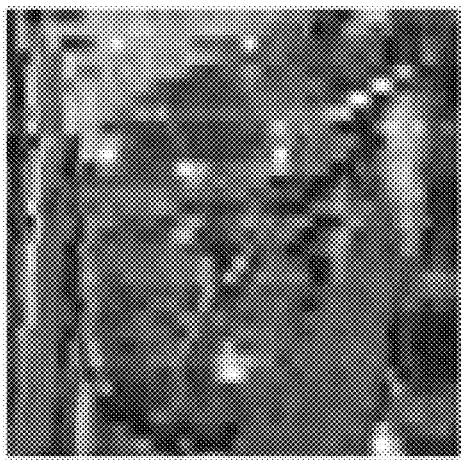

Based on the first probability map 1420, a preliminary region 1409 representative of the right kidney (denoted as a bounding box) was segmented from the target image 1400 as illustrated in FIG. 14D. The pixel values of the preliminary region 1409 were normalized to a range [−1, 1], and the normalized preliminary region was further resampled to generate a preprocessed preliminary region 1440 as shown in FIG. 14E. The size of the preprocessed preliminary region 1440 is 144*144*208, and the image resolution of the preprocessed preliminary region 1440 is [1 mm, 1 mm, 1 mm].

Figure 14F:
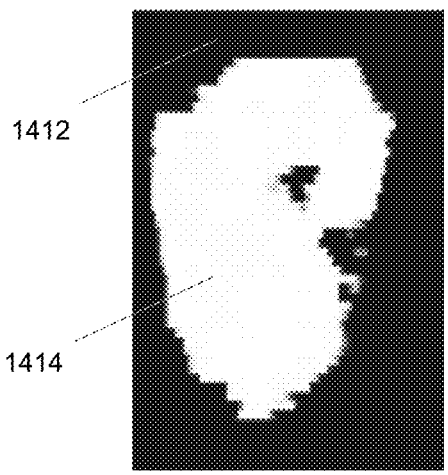

In some embodiments, the image resolution of the preprocessed preliminary region 1440 may be equal to an image resolution of a second ROI segmentation model as described in connection with FIG. 5. The preprocessed preliminary region 1440 was inputted into the second ROI segmentation model to generate a second probability map 1450 of the right kidney as illustrated in FIG. 14F. In the second probability map 1450, probability values of pixels in a white region 1414 may be close to 1, and probability values of pixels in a black region 1412 may be close to 0. The white region 1414 may be regarded as the right kidney according to the second probability map 1450. The size of the second probability map 1450 is 144*144*208, and the image resolution of the second probability map 1450 is [1 mm, 1 mm, 1 mm].

Figure 14G:
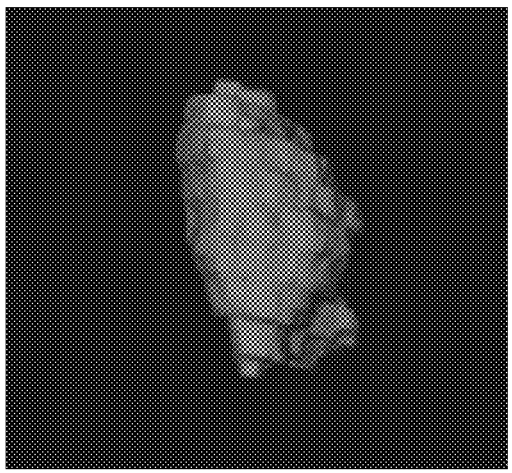
Figure 14H:
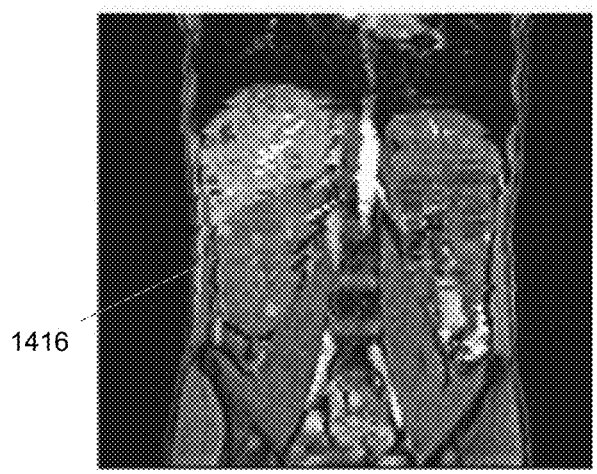
Figure 14I:
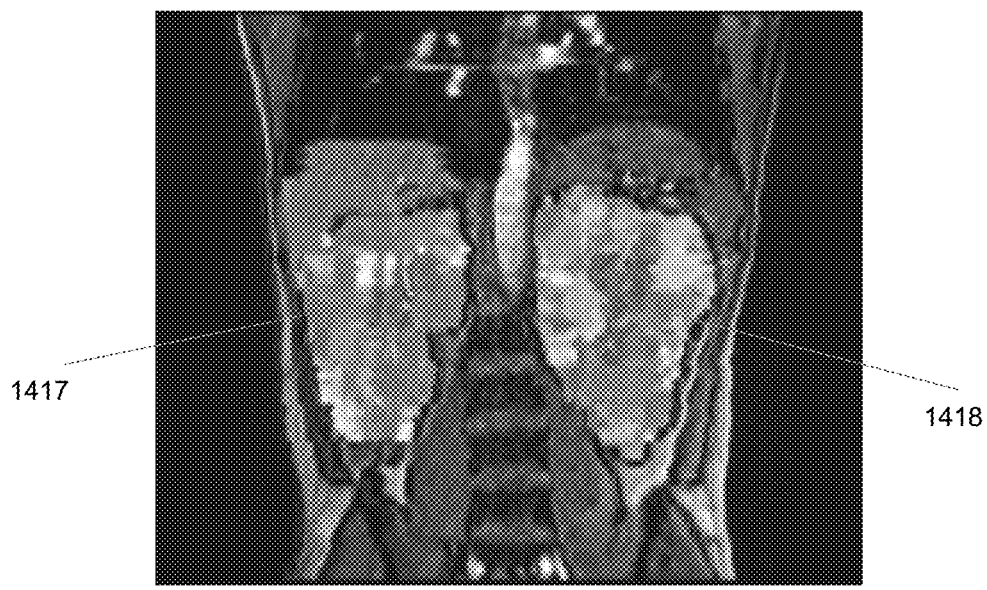

As shown in FIG. 14G, a 3D image 1460 of the right kidney was generated by resampling ROI segmented from the preliminary region 1409, wherein the 3D image 1460 has a same image resolution as the target image 1400. Optionally, as shown in FIG. 14H, a region 1416 of the right kidney was annotated from the target image 1400 based on the second probability map 1450. In some embodiments, the 3D image 1460 or the region 1416 may be regarded as the target region representative of the right kidney. In some embodiments, the left kidney and the right kidney may both be segmented from a target image. For example, as shown in FIG. 14I, the right kidney 1417 and the left kidney 1418 were segmented from a target image 1470.

FIGS. 15A to 15H are schematic diagrams illustrating an exemplary process of liver segmentation according to some embodiments of the present disclosure.

Figure 15A:
FIGS. 15A to 15H are schematic diagrams illustrating an exemplary process of liver segmentation according to some embodiments of the present disclosure.
Figure 15B:

FIG. 15A illustrates a target image 1500, which includes a liver to be segmented and was captured by a CT scanner. The size of the target image 1500 is 512*512*594, and the image resolution of the target image 1500 is [1.172 mm, 1.172 mm, 1.5 mm]. The target image 1500 was resampled and normalized to generate a preprocessed target image 1510 as shown in FIG. 15B. The size of the preprocessed target image 1510 is 112*112*160 and an image resolution of the preprocessed target image 1510 is [6 mm, 6 mm, 6 mm].

Figure 15C:
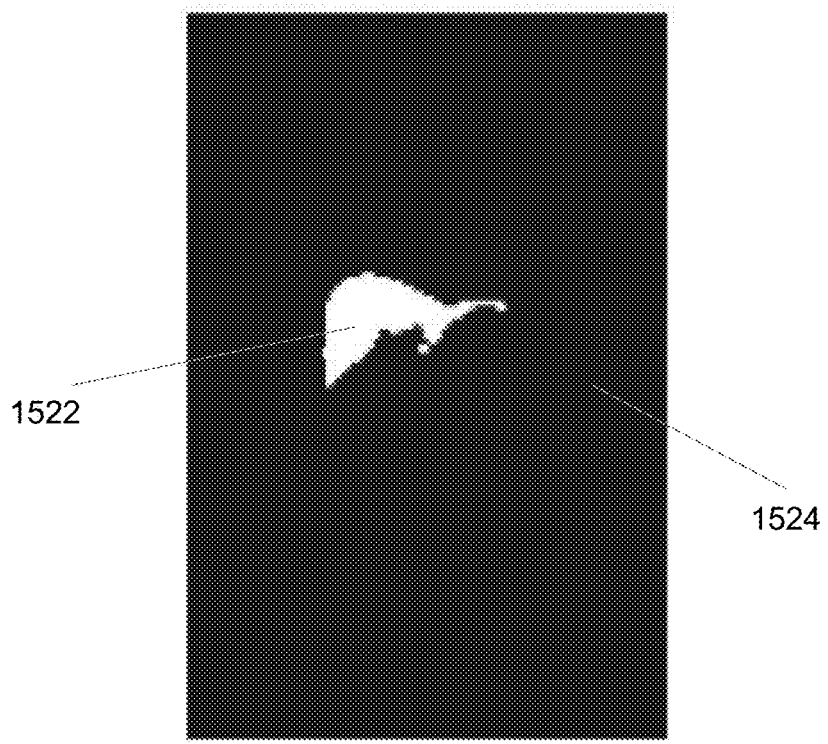

In some embodiments, the preprocessed target image 1510 was inputted into a first ROI segmentation model corresponding to an image resolution [6 mm, 6 mm, 6 mm] to generate a first probability map 1520 of the liver as illustrated in FIG. 15C. In the first probability map 1520, probability values of pixels in a white region 1522 may be close to 1, and probability values of pixels in a black region 1524 may be close to 0 (e.g., less than $10^{-6}$).

Figure 15D:
Figure 15E:
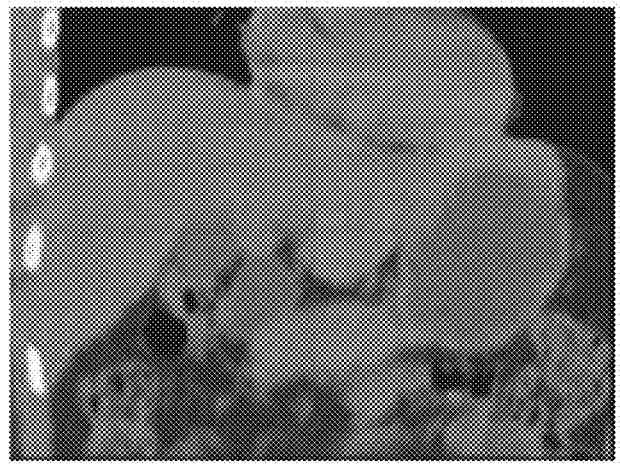

As illustrated in FIG. 15D, a preliminary region 1530 representative of the liver was segmented from the target image 1500 based on the first probability map 1520. The preliminary region 1530 was resampled to generate a resampled preliminary region having an image resolution [1 mm, 1 mm, 1 mm], and the pixel values of the resampled preliminary region were normalized to a range [−1, 1] to generate a preprocessed preliminary region 1540 as shown in FIG. 15E. The size of the preprocessed preliminary region 1540 is 1256*256*192.

Figure 15F:
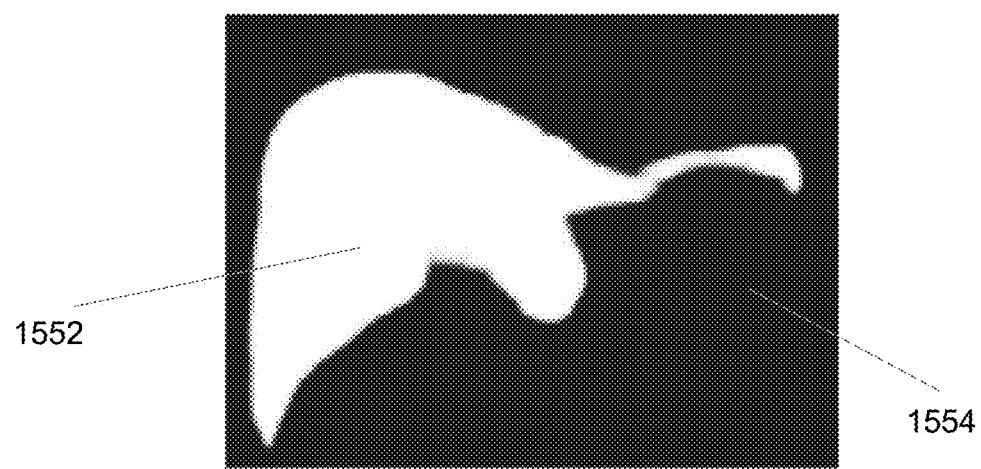

In some embodiments, the preprocessed preliminary region 1540 was inputted into a second ROI segmentation model corresponding to an image resolution [1 mm, 1 mm, 1 mm] to generate a second probability map 1550 of the liver as illustrated in FIG. 15F. In the second probability map 1550, probability values of pixels within a white region 1552 may be close to 1, and probability values of pixels within a black region 1554 may be close to 0. The size of the second probability map 1550 is 256*256*192, and the image resolution of the second probability map 1550 is [1 mm, 1 mm, 1 mm].

Figure 15G:
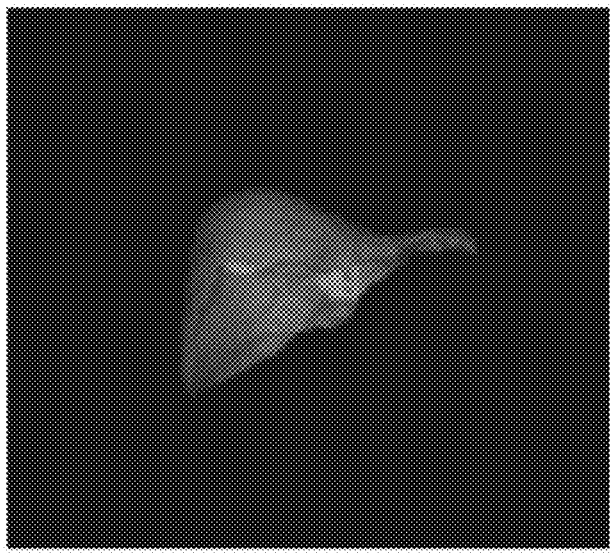
Figure 15H:

As shown in FIG. 15G, a 3D image 1560 of the liver was generated by resampling the ROI segmented from the preliminary region 1530, wherein the 3D image 1560 has a same image resolution as the target image 1500. Optionally, as shown in FIG. 15H, a region 1572 of the liver was annotated from the target image 1500 based on the second probability map 1550. In some embodiments, the 3D image 1560 or the region 1572 may be regarded as the target region representative of the liver.

Figure 17A:
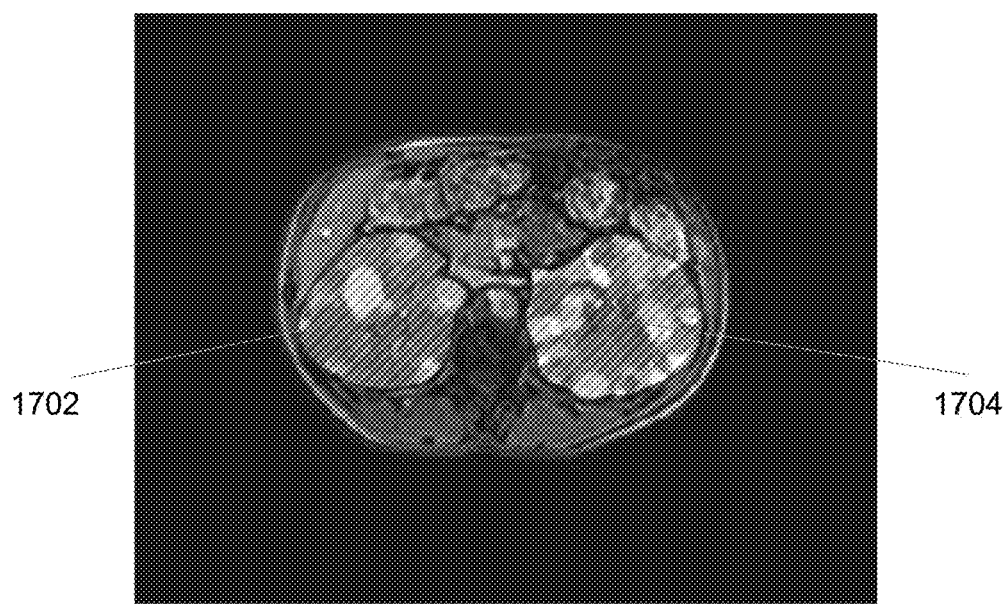
FIG. 17A is a schematic diagram illustrating an exemplary MR slice image of a first patient with a polycystic kidney disease according to some embodiments of the present disclosure.

FIG. 17A is a schematic diagram illustrating an exemplary MR slice image 1700 of a first patient with a polycystic kidney disease according to some embodiments of the present disclosure. A left kidney 1704 and a right kidney 1702 were segmented from the MR slice image 1700 by performing an exemplary process (e.g., the process 500) for image segmentation disclosed herein.

Figure 17B:
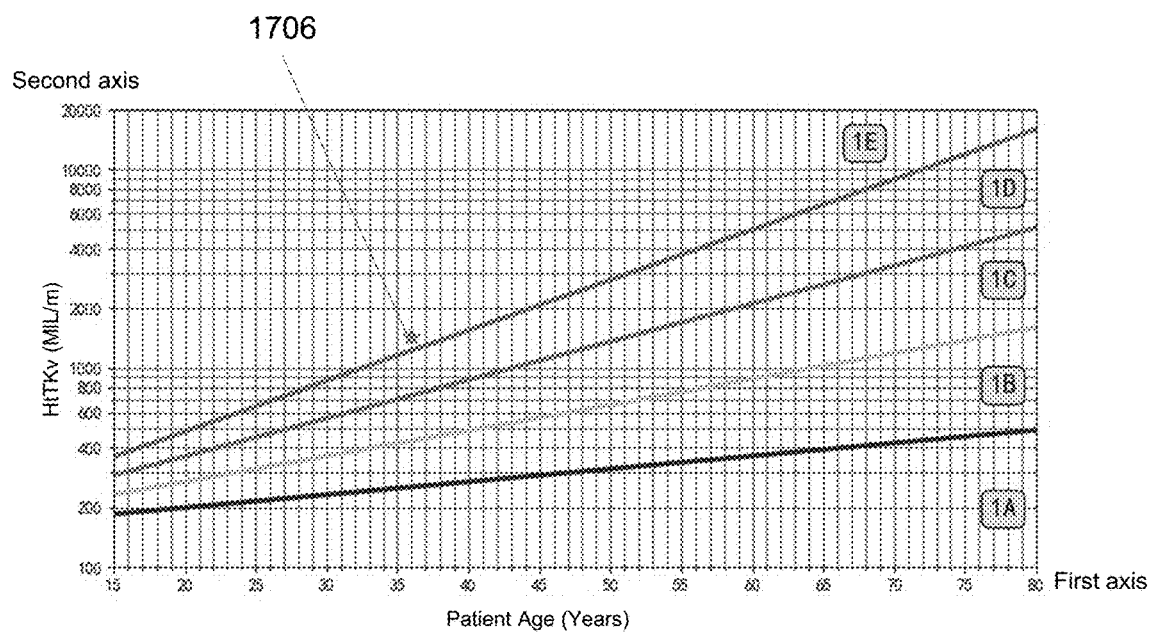
FIG. 17B is a schematic diagram illustrating an exemplary data point corresponding to the first patient in FIG. 17A in a classification chart regarding polycystic kidney disease according to some embodiments of the present disclosure.

In some embodiments, the TKV of the left kidney 1704 and the right kidney 1702 may be determined, and the functionality of the kidneys of the first patient may be classed according to a classification chart regarding polycystic kidney disease as described elsewhere in this disclosure (e.g., 540 and the relevant descriptions). For example, FIG. 17B illustrates an exemplary data point 1706 corresponding to the first patient in a classification chart regarding polycystic kidney disease. The functionality of the kidneys of the first patient may be classed into class 1E according to FIG. 17B.

Figure 18A:
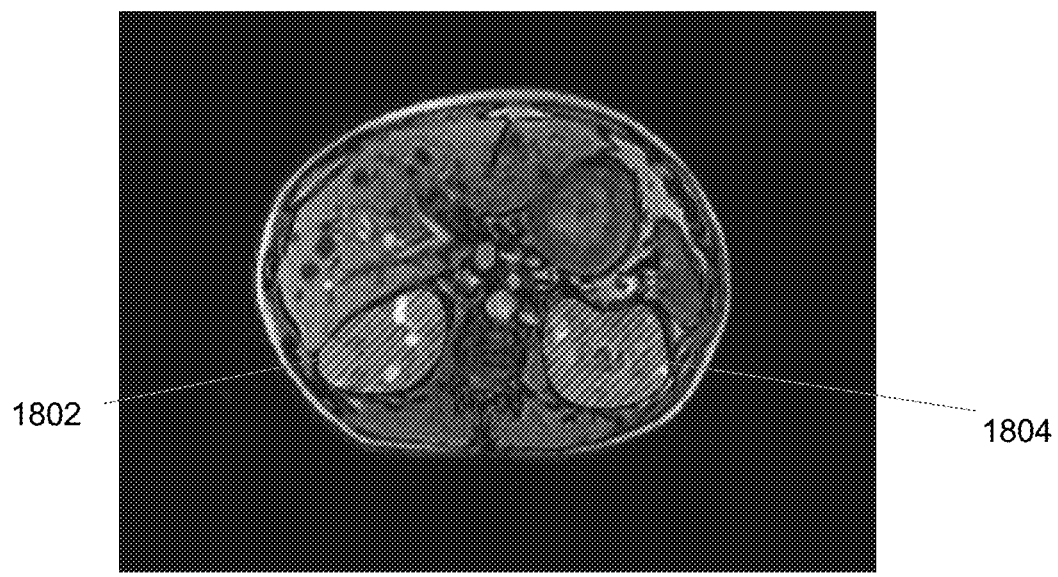
FIG. 18A is a schematic diagram illustrating an exemplary MR slice image of a second patient with a polycystic kidney disease according to some embodiments of the present disclosure.
Figure 18B:
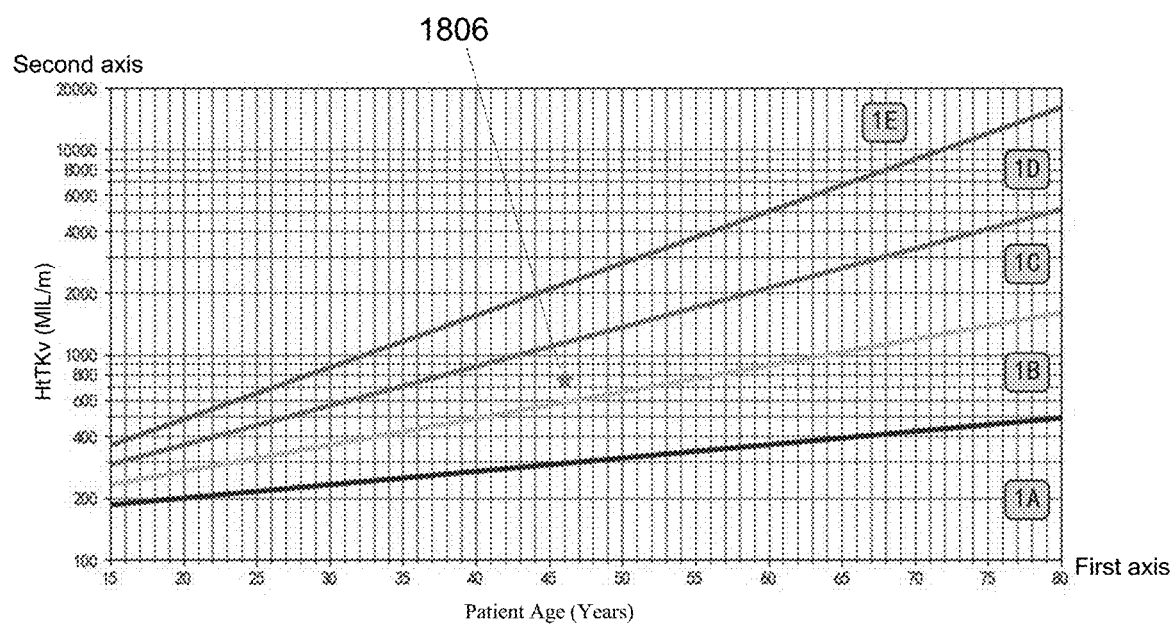
FIG. 18B is a schematic diagram illustrating an exemplary data point corresponding to the second patient in FIG. 18A in a classification chart regarding polycystic kidney disease according to some embodiments of the present disclosure.

FIG. 18A is a schematic diagram illustrating an exemplary MR slice image 1800 of a second patient with a polycystic kidney disease according to some embodiments of the present disclosure. A left kidney 1804 and a right kidney 1802 were segmented from the MR slice image 1800 by performing an exemplary process (e.g., the process 500) for image segmentation disclosed herein. FIG. 18B illustrates an exemplary data point 1806 corresponding to the second patient in a classification chart regarding polycystic kidney disease. The functionality of the kidneys of the second patient may be classed into class 1C according to FIG. 18B.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for image segmentation, comprising:
   at least one storage medium including a set of instructions; and
   at least one processor configured to communicate with the at least one storage medium, wherein when executing the set of instructions, the at least one processor is configured to direct the system to perform operations including:
   obtaining a target image including a region of interest (ROI);
   segmenting, from the target image, a preliminary region representative of the ROI using a first ROI segmentation model corresponding to a first image resolution; and
   segmenting, from the preliminary region, a target region representative of the ROI using a second ROI segmentation model corresponding to a second image resolution, wherein
   the first image resolution is lower than the second image resolution, and
   at least one model of the first ROI segmentation model or the second ROI segmentation model includes a plurality of convolutional layers, the plurality of convolutional layers at least including a first convolutional layer and a second convolutional layer downstream to the first convolutional layer, a count of input channels of the first convolutional layer is greater than a count of output channels of the first convolutional layer, and a count of input channels of the second convolutional layer is smaller than a count of output channels of the second convolutional layer.

2. The system of claim 1, wherein the at least one processor is further configured to direct the system to perform the operations including:
determining, based on the target region, a parameter value indicative of a physiological condition of the ROI; and
evaluating, based on the parameter value, the physiological condition of the ROI.

3. The system of claim 2, wherein the ROI includes a polycystic kidney, the parameter value includes a volume of the polycystic kidney, and
to evaluate a physiological condition of the ROI based on the volume of the ROI, the at least one processor is further configured to direct the system to perform the operations including:
classifying, based at least in part on the volume of the polycystic kidney, a functionality of the polycystic kidney.

4. The system of claim 1, wherein to segment a preliminary region representative of the ROI from the target image, the at least one processor is further configured to direct the system to perform the operations including:
preprocessing the target image;
segmenting, from the preprocessed target image, the ROI by applying the first ROI segmentation model to the preprocessed target image; and
segmenting, from the target image, the preliminary region based on the segmented ROI in the preprocessed target image.

5. The system of claim 4, wherein to preprocess the target image, the at least one processor is further configured to direct the system to perform the operations including:
generating a resampled target image having the first image resolution by resampling the target image; and
generating the preprocessed target image by normalizing the resampled target image.

6. The system of claim 1, wherein to segment a target region representative of the ROI from the preliminary region, the at least one processor is further configured to direct the system to perform the operations including:
preprocessing the preliminary region;
segmenting, from the preprocessed preliminary region, the ROI by applying the second ROI segmentation model to the preprocessed preliminary region; and
generating the target region by resampling the segmented ROI in the preprocessed preliminary region, the target region and the target image having a same image resolution.

7. The system of claim 6, wherein to preprocess the preliminary region, the at least one processor is further configured to direct the system to perform the operations including:
generating a resampled preliminary region having the second image resolution by resampling the preliminary region; and
generating the preprocessed preliminary region by normalizing the resampled preliminary region.

8. The system of claim 1, wherein the at least one model is one of a V-net model, a U-net model, an AlexNet model, an Oxford Visual Geometry Group (VGG) model, or a ResNet model.

9. The system of claim 1, wherein the count of input channels of the first convolutional layer is equal to the count of output channels of the second convolutional layer.

10. The system of claim 1, wherein the at least one model further includes a third convolutional layer between the first convolutional layer and the second convolutional layer, and a count of output channels of the third convolutional layer is equal to a count of input channels of the third convolutional layer.

11. The system of claim 1, wherein the at least one processor is further configured to direct the system to perform the operations including:
determining, in the at least one storage device, a first memory space and a second memory space based on the plurality of convolutional layers, wherein
the plurality of convolutional layers include a fourth convolutional layer and a fifth convolutional layer adjacent to each other, and
during the application of the at least one model,
input data of the fourth convolutional layer are stored in the first memory space,
output data of the fourth convolutional layer are stored in the second memory,
input data of the fifth convolutional layer are stored in the second memory space, and
output data of the fifth convolutional layer are stored in the first memory.

12. The system of claim 11, wherein the at least one model includes at least one skip-connection, and data relating to the at least one skip-connection is stored in at least one of the first memory space or the second memory space.

13. The system of claim 11, wherein the preliminary model includes at least one of a V-net model, a U-net model, an AlexNet model, an Oxford Visual Geometry Group (VGG) model, or a ResNet model.

14. A system for training a region of interest (ROI) segmentation model corresponding to a target image resolution, comprising:
at least one storage medium storing a set of instructions; and
at least one processor configured to communicate with the at least one storage medium, wherein when executing the set of instructions, the at least one processor is configured to direct the system to perform operations including:
obtaining at least one training image, each of the at least one training image including an annotated ROI and having the target image resolution;
obtaining a preliminary model including a plurality of convolutional layers; and
generating the ROI segmentation model corresponding to the target image resolution by training the preliminary model using the at least one training image, wherein
the plurality of convolutional layers include at least a first convolutional layer and a second convolutional layer downstream to the first convolutional layer, and
a count of input channels of the first convolutional layer is greater than a count of output channels of the first convolutional layer, and a count of input channels of the second convolutional layer is smaller than a count of output channels of the second convolutional layer.

15. The system of claim 14, wherein to acquire at least one training image, the at least one processor is further configured to direct the system to perform the operations including:
obtaining at least one image including an annotated ROI and having an image resolution different from the target image resolution;
generating at least one resampled image having the target image resolution by resampling the at least one image; and generating the at least one training image by normalizing the at least one resampled image.

16. The system of claim 14, wherein the count of input channels of the first convolutional layer is equal to the count of the output channels of the second convolutional layer.

17. The system of claim 14, wherein the plurality of convolutional layers further includes a third convolutional layer between the first convolutional layer and the second convolutional layer, and a count of output channels of the third convolutional layer is equal to a count of input channels of the third convolutional layer.

18. A method for image segmentation implemented on a computing device having at least one processor and at least one storage device, the method comprising:

obtaining a target image including a region of interest (ROI);

segmenting, from the target image, a preliminary region representative of the ROI using a first ROI segmentation model corresponding to a first image resolution; and segmenting, from the preliminary region, a target region representative of the ROI using a second ROI segmentation model corresponding to a second image resolution, wherein the first image resolution is lower than the second image resolution, at least one model of the first ROI segmentation model or the second ROI segmentation model includes at least a first convolutional layer and a second convolutional layer downstream to the first convolutional layer, a count of input channels of the first convolutional layer is greater than a count of output channels of the first convolutional layer, and a count of input channels of the second convolutional layer is smaller than a count of output channels of the second convolutional layer.

19. The method of claim 18, wherein the count of input channels of the first convolutional layer is equal to the count of output channels of the second convolutional layer.

20. The method of claim 18, wherein the at least one model further includes a third convolutional layer between the first convolutional layer and the second convolutional layer, and a count of output channels of the third convolutional layer is equal to a count of input channels of the third convolutional layer.

\* \* \* \* \*